United States Patent [19]

Chatterjee et al.

[11] Patent Number: 5,428,038

[45] Date of Patent: Jun. 27, 1995

[54] BENZOPYRANONES, A METHOD FOR PRODUCING THEM AND USES THEREFOR

[75] Inventors: Shyam S. Chatterjee, Karlsruhe; Michael Nöldner, Leopoldshafen; Hermann Hauer; Egon Koch, both of Karlsruhe, all of Germany

[73] Assignee: Dr. Willmar Schwabe GmbH & Co., Germany

[21] Appl. No.: 133,017

[22] PCT Filed: Apr. 2, 1992

[86] PCT No.: PCT/EP92/00739

§ 371 Date: Oct. 8, 1993

§ 102(e) Date: Oct. 8, 1993

[87] PCT Pub. No.: WO92/18493

PCT Pub. Date: Oct. 29, 1992

[30] Foreign Application Priority Data

Apr. 11, 1991 [DE] Germany .................. 41 11 861.8

[51] Int. Cl.$^6$ ................ A61K 31/495; A61K 31/445; C07D 409/00; C07D 311/04
[52] U.S. Cl. .................... 514/253; 514/320; 514/326; 544/376; 546/196; 546/207; 549/399
[58] Field of Search ............... 544/376; 546/207, 196; 514/253, 326, 320; 549/399

[56] References Cited

U.S. PATENT DOCUMENTS

| | | | |
|---|---|---|---|
| 4,382,943 | 5/1983 | Winter et al. | 424/267 |
| 4,558,130 | 12/1985 | Buckler et al. | 546/66 |
| 4,569,994 | 2/1986 | Griffith | 544/150 |
| 4,749,798 | 6/1988 | Gandolfi et al. | 549/283 |
| 5,072,007 | 12/1991 | Fukuoka et al. | 549/399 |
| 5,248,784 | 9/1993 | Ohyama et al. | 549/399 |

FOREIGN PATENT DOCUMENTS 0175541 3/1986 European Pat. Off. .

OTHER PUBLICATIONS

Greenamyre et al, Neurobiology of Aging vol. 10, p. 593 (1989).
Sunahara et al, British Journal of Psychiatry (1993), 163 (suppl. 22) 31–38.
International Search Report.
List of patent family for EP-A-0043-535.
International Search Report, dated Jun. 30, 1992.
International Preliminary Examination Report, dated Mar. 8, 1993.
Seeman; Controversies in Neurology, Arch Neurol vol. 50, 1993, p. 1093.
Journal of Medicinal Chemistry, J. I. Degraw et al., vol. 11, No. 2, Feb., 1968.
Chemical Abstracts, V. A. Zagorevski et al., vol. 72, No. 7, Feb. 1970.
Chemical & Pharmaceutical Bulletin, K. Aihara et al., vol. 38, No. 3, Mar. 1990.
Journal of Biological Chemistry, N. Harada et al., vol. 259, No. 5, Mar. 1984.
Journal of the Chemical Society, Chemical Communications, S. V. Kessar et al., No. 7, Apr. 1983.

Primary Examiner—Cecilia Tsang
Attorney, Agent, or Firm—Frost & Jacobs

[57] ABSTRACT

Novel 2H-1-benzopyran-2-ones (coumarin derivatives) of the general formula (I) are provided:

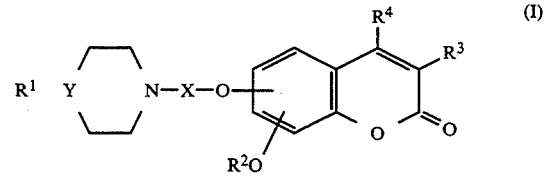

wherein $R^1$, $R^2$, $R^3$, $R^4$, X and Y are defined as in the specification, and the addition compounds thereof with physiologically compatible acids, intermediates and methods for the preparation thereof. The coumarin compounds possess a neuroprotective and anti-allergic action.

5 Claims, No Drawings

BENZOPYRANONES, A METHOD FOR PRODUCING THEM AND USES THEREFOR

This application is a 371 application of PCT/EP92/00739, filed Apr. 2, 1992.

The invention relates to benzopyranones, whose basic structure may be derived from coumarin, a method for the production of these compounds, including the reactive intermediates then produced, and furthermore medicaments, which contain these compounds.

The central nervous system (CNS) of mammals possesses high concentrations of excitatory amino acids (EAA) such as glutamate, aspartate, and homocysteate having the function of neurotransmitters and cooperating with specific receptors.

The three types of receptors which have been best characterized so far are those named after their selective agonists, namely N-methyl-D-aspartate (NMDA), kainate (KA) and quisqualate (QA) receptors. All three receptors may be activated by glutamate and aspartate. It is known that as a consequence of a cerebral ischemia glutamate is liberated in major quantities, and inter alia binds to the NMDA receptor complex and is responsible for an increased input of calcium and to an increased release of intracellular calcium into the neuronal cells. The NMDA receptor complex inter alia has binding sites for glutamate, glycine, phencyclidine, $Mg^{2+}$ and $Zn^{2+}$. Since a series of pharmacological investigations have indicated that modulators of neurotransmission mediated by NMDA receptors may influence cytotoxicity mediated by NMDA, various different selective NMDA antagonists already have been investigated as regards their possible neuroprotective action (see G. L. Collingridge, R. A. J. Lester: "Excitatory Amino Acid Receptors in the Vertebrate Central Nervous System", Pharamacol. Rev. 40, No. 2, pp. 143–210 (1989); L. Turski: "N-Methyl-D-aspartat-Rezeptorkomplex", in Arzneim.-Forsch/Drug Res. 40 (I), No. 5, pp. 511–514 (1990)). Owing to the undesired side effects of known NMDA antagonists there is still a substantial need for the provision of novel compounds with an NMDA antagonistic effect and which exhibit less side effects or have a different spectrum of action.

Therefore one object of the invention is to provide new compounds which have minimum toxicity while nevertheless having an NMDA antagonistic action and able to be utilized as medicament components, more particularly for the therapy of chronic neurodegenerative diseases in order to prevent neurodegeneration in the CNS caused by ischemia or trauma or by other pathological alterations and to prevent the occurrence of convulsions or at least to reduce the same. Furthermore the novel compounds may have additionally a broad antiallergic and anti-inflammatory spectrum with a prolonged period of action; in this case, however, such compounds are to be orally administrable.

This object is attained by the compounds and the methods in accordance with the invention and by the use of these compounds as a medicament which has a neuroprotective, anticonvulsive, anti-epileptic and, optionally, an anti-allergic and anti-inflammatory action.

The invention thus relates to:
2H-1-benzopyran-2-ones of the general formula I,

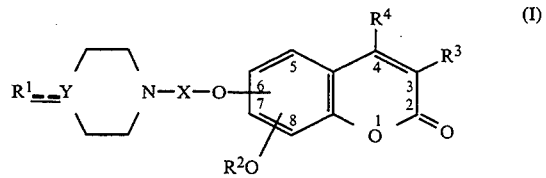

wherein:
- X denotes an alkylene group with 2 to 5 C. atoms or a 2-hydroxypropylene group,
- Y denotes a nitrogen atom, a CH— group, a COH— group or a carbon atom,
- $R^1$ denotes a phenyl, benzhydryl, benzhydrylidene, benzyl, diphenylhydroxymethyl, pyridinyl or pyrimidinyl radical, which is optionally substituted with respectively one or two $C_1$–$C_5$ alkyl groups, with respectively one or two halogen atoms, with halogen and simultaneously $C_1$–$C_5$ alkyl, with perfluoroalkyl with 1 to 3 C. atoms, $C_1$–$C_5$ alkoxy, methylenedioxy, hydroxy or nitro,
- $R^2$ denotes a straight chained or branched alkyl radical with 1 to 5 C. atoms or a cycloalkyl radical with 4 to 6 C. atoms,
- $R^3$ denotes a hydrogen atom, an alkyl group with 1 to 4 C. atoms or a phenyl radical,
- $R^4$ denotes a hydrogen atom, an alkyl group with 1 to 4 C. atoms, a phenyl radical or a trifluoromethyl radical or
- $R^3$ and $R^4$ jointly denote a polymethylene chain —$(CH_2)_n$— with n equal to 3 or 4, and the addition compounds thereof with physiologically compatible acids.

The compounds in accordance with the invention are novel. Compounds are known which are derived from 7-hydroxycoumarin (umbelliferone), which however have a second alkoxy group corresponding to the $R^2O$— radical of the general formula I missing. Such umbelliferone derivatives are described in the German patent publication 2,123,924 C3 and the European patent publication 0,171,645 A1, furthermore as an anti-edematic (in the case of the German patent publication 2,123,924 C3 only), anti-inflammatory and anti-allergic substances for use in medicaments, more particularly antihistaminics. Furthermore the European patent publication 0,175,541 A1 describes similar umbelliferone derivatives with an anti-psychotic and anxiolytic action, while in the U.S. Pat. No. 4,569,994 such substances with an anti-hypoxic effect are described.

Finally the European patent publication 0,043,535 B1 discloses tricyclic compounds of the general formula I, in the case of which however $R^1$ in every case denotes an optionally substituted amino radical and which consequently are substantially different to the compounds in accordance with the invention. These known compounds are said to be anti-allergic, anti-edematic and anti-phlogistic in their action and are to be preferentially used for combatting asthma, hay fever and urticaria.

In the light of this prior art it was surprising for those skilled in the art that the compounds in accordance with the invention of the general formula I have an NMDA-antagonistic and neuroprotective action, some of them additionally being effective anti-allergically and anti-inflammatorily.

In the case of the compounds in accordance with the invention of the general formula I it is possible for the two alkoxy radicals attached to the anellated benzene ring of the coumarin skeleton, that is to say the R²O— radical and the radical with the general formula II $$R^1{=}Y\diagup\overset{\diagdown}{\underset{\diagup}{N-X-O-}}\diagdown \quad (II)$$

wherein R¹, Y and X have the above noted meanings, to be joined at the positions 5 to 8 of the coumarin structure in any desired combination. In this case such compounds of the general formula I are preferred, in which the radical II is attached at the 6 or 7 position and the alkoxy radical R²O— is attached at the 7 or 6 position, thus still unoccupied, of 2H-1-benzopyran-2-one.

In accordance with the invention compounds are preferred having the said general formula I in the case of which:

X denotes an alkylene group with 2 to 5 C. atoms,
Y denotes N— or CH—,
R¹ denotes a phenyl or diphenylhydroxymethyl radical with optional substitution by a halogen atom, methyl, methoxy, ethoxy or hydroxy,
R² denotes methyl or ethyl
R³ denotes a hydrogen atom, a methyl or phenyl group,
R⁴ denotes a hydrogen atom, methyl, propyl, isopropyl or
R³ and
R⁴ jointly denote a polymethylene chain —(CH₂)ₙ— in which n is equal to 3 or 4, and the addition compounds thereof with physiologically compatible acids.

Owing to their pharmacological action particularly preferred compounds are those of the examples 1 to 4, 7, 14, 17, 29, 33, 35, 41 to 49, 52, 54 to 60 and 66, that is to say 7-methoxy-6-[3-(4-phenyl-1-piperazinyl)propoxy]-2H-1-benzopyran-2-one, 6-methoxy-7-[3-(4-phenyl-1-piperazinyl)-propoxy]-2H-1-benzopyran-2-one, 7-ethoxy-6-[3-(4-phenyl-1-piperazinyl)propoxy]-2H-1-benzopyran-2-one, 6-ethoxy-7-[3-(4-phenyl-1-piperazinyl)propoxy]-2H-1-benzopyran-2-one, 7-ethoxy-6-{3-[4-(2-methoxyphenyl)-1-piperazinyl]-propoxy}-2H-1-benzopyran-2-one, 7-{3-[4-(bis(4-fluorophenyl)-hydroxymethyl)-1-piperidinyl]propoxy)}-6-methoxy-2H-1-benzopyran-2-one, 7-{3-[4-(diphenylhydroxymethyl)-1-piperidinyl]-propoxy}-6-methoxy-2H-1-benzopyran-2-one, 7-methoxy-3,4-dimethyl-6-[3-(4-phenyl-1-piperidinyl)propoxy]-2H-1-benzopyran-2-one, 7-methoxy-6-[3-(4-phenyl-1-piperazinyl)propoxy]-4-propyl-2H-1-benzopyran-2-one, 7-methoxy-4-(1-methylethyl)-6-[3-(4-phenyl-1-piperazinyl)propoxy]-2H-1-benzopyran-2-one, 7-methoxy-4-methyl-3-phenyl-6-[3-(4-phenyl-1-piperazinyl)propoxy]-2H-1-benzopyran-2-one, 7,8,9,10-tetrahydro-3-methoxy-2-[3-(4-phenyl-1-piperazinyl)-propoxy]-6H-dibenzo[b,d]pyran-6-one, 7,8,9,10-tetrahydro-3-methoxy-2-[3-(4-phenyl-1-piperidinyl)-propoxy]-6H-dibenzo[b,d]pyran-6-one, 2,3-dihydro-7-methoxy-8-[2-(4-phenyl-1-piperazinyl)ethoxy]cyclopenta[c][1]benzopyran-4(1H)-one, 2,3-dihydro-7-methoxy-8-[3-(4-phenyl-1-piperazinyl)propoxy]cyclopenta[c][1]benzopyran-4(1H)-one, 2,3-dihydro-7-methoxy-8-[4-(4-phenyl-1-piperazinyl)butyloxy]cyclopenta[c][1]benzopyran-4(1H)-one, 2,3-dihydro-7-methoxy-8-[5-(4-phenyl-1-piperazinyl)pentyl-oxy]cyclopenta[c][1]-benzopyran-4(1H)-one, 2,3-dihydro-7-methoxy-8-[2-(4-phenyl-1-piperidinyl)ethoxy]cyclopenta[c][1]-benzopyran-4(1H)-one, 2,3-dihydro-7-methoxy-8-[3-(4-phenyl-1-piperidinyl)-propoxy]cyclopenta[c][1]benzopyran-4(1H)-one, 8-{3-[4-(4-fluorophenyl)-1-piperazinyl]propoxy}-2,3-dihydro-7-methoxy-cyclopenta[c][1]benzopyran-4(1H)-one, 2,3-dihydro-7-methoxy-8-{3-[4-(2-methoxyphenyl)-1-piperazinyl]-propoxy}cyclopenta[c][1]benzopyran-4(1H)-one, 2,3-dihydro-7-methoxy-8-{3-[4-(3-methoxyphenyl)-1-piperazinyl]propoxy}cyclopenta[c][1]benzopyran-4-(1H)-one, 2,3-dihydro-7-methoxy-8-{3-[4-(4-methoxyphenyl)-1-piperazinyl]propoxy}cyclopenta[c][1]benzopyran-4(1H)-one, 8-{3-[4-(2-ethoxyphenyl)-1-piperazinyl]propoxy}-2,3-dihydro-7-methoxy-cyclopenta[c][1]benzopyran-4(1H)-one, 8-{3-[4-(2-chlorophenyl)-1-piperazinyl]propoxy}-2,3-dihydro-7-methoxy-cyclopenta[c][1]benzopyran-4(1H)-one, 2,3-dihydro-7-methoxy-8-{3-[4-(2-methylphenyl)-1-piperazinyl]propoxy}cyclopenta[c][1]benzopyran-4(1H)-one, 2,3-dihydro-8-{3-[4-(2-hydroxyphenyl)-1-piperazinyl]propoxy}-7-methoxy-cyclopenta[c][1]benzopyran-4(1H)-one, 8-{3-[4-(2-fluorophenyl)-1-piperazinyl]propoxy}-2,3-dihydro-7-methoxy-cyclopenta[c][1]benzopyran-4(1H)-one.

In the method for the production of compounds of the general formula I either a) a compound of the general formula III $$\text{(III)}$$

wherein X, R², R³ and R⁴ have the above noted meanings and A denotes a leaving group selected from the group consisting essentially of chlorine, bromine, iodine, alkylsulfonyloxy, and trifluoromethylsulfonyloxy and phenylsulfonyloxy which is optionally substituted with alkyl, nitro or halogen, is reacted with a compound of the general formula V $$\text{(V)}$$

wherein Y and R¹ have the above noted meanings, the compound of the general formula V also optionally being present in the form of its hydrochloride or another acid addition salt, or b) a compound of the general formula VI, $$\text{(VI)}$$

wherein R², R³ and R⁴ have the above noted meanings is reacted with a compound of the general formula VII,

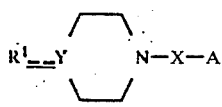 (VII)

wherein A, X, Y and R¹ have the above noted meanings,
whereafter both in the case of method (a) and also in the case of method (b) the obtained products are optionally converted into their physiologically compatible acid addition compounds.

The reactions according to method (a) or method (b) may be performed in a conventional manner. Thus for instance in accordance with the German patent 2,123,924 the reaction of 7-hydroxy-3,4-dimethyl-coumarin with 1-(3-chloropropyl)-4-benzyl-piperazine is disclosed. In order to bind the acid HA produced, wherein A denotes one of the above noted leaving groups, these reactions take place in the presence of a base such as an alkali metal or alkaline earth metal carbonate, hydrogencarbonate, hydride, alcoholate, hydroxide or of a tertiary amine, in which respect preferably alkali metal carbonates and hydrogencarbonates or hydrides are utilized. The reactions are preferably performed in the presence of solvents inert with respect to the reactants. Solvents which are well suited in this respect are alkanols, aromatic solvents such as toluene, xylene or the like, or dipolar aprotic solvents such as aliphatic or cycloaliphatic ethers, carboxylic acid dialkylamides, tetraalkylureas, ketones and sulfoxides. It is preferred to use alkanols with 1 to 5 C atoms or dimethylformamide. If desired it is possible to use 0.02 to 0.5 equivalent of an alkali metal or alkaline earth metal iodide and preferably 0.05 to 0.2 equivalent of potassium iodide as an added catalyst. The reaction may be performed at a temperature, which is between room temperature and 130° C., although it is preferred to operate at a temperature between room temperature and 100° C. or, in the case of solvents with low boiling point, near the boiling point thereof. Oxidative by-products may be avoided by operation under a protective gas atmosphere, for instance nitrogen or argon. The reactions are performed under normal pressure or in sealed vessels at pressures up to 10⁷ Pa (100 bar).

Those compounds of the general formula I, in the case of which X denotes a 2-hydroxypropylene group, may in accordance with a further embodiment of the method in accordance with the invention be produced in such a manner that an epoxide compound of the general formula IV

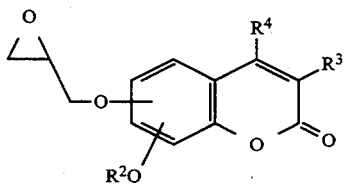 (IV)

wherein R², R³ and R⁴ have the above noted meanings, is reacted with a compound of the general formula V,

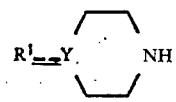 (V)

wherein R¹ and Y have the above noted meanings, the compounds of the general formula V optionally being present in the form of their hydrochloride or of another acid addition salt.

Unlike the case of the forms (a) and (b) of the method in the case of this form thereof no leaving group A is necessary, for which reason no acid is produced and the addition of a base is unnecessary. The solvents, the catalysts, the temperatures, the pressures and the other parameters of the method are on the other hand the same in all forms of the method.

The production of the compounds in accordance with the invention of the general formula I may be performed via reactive intermediates of the general formula XI

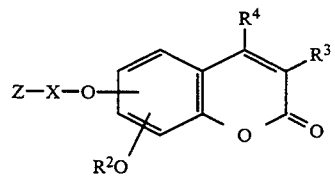 (XI)

wherein
R² denotes a straight chained or branched alkyl radical with 1 to 5 C atoms or a cycloalkyl radical with 4 to 6 C atoms,
R³ denotes a hydrogen atom, an alkyl group with 1 to 4 C atoms or a phenyl radical,
R⁴ denotes a hydrogen atom, an alkyl group with 1 to 4 C atoms, a phenyl radical or a trifluoromethyl radical or
R³ and
R⁴ jointly denote a polymethylene chain —(CH₂)ₙ— with n equal to 3 or 4
X denotes an alkylene group with 2 to 5 C atoms and
Z denotes a hydroxyl or methanesulfonyloxy group, a halogen atom or
Z—X jointly denote a hydrogen atom or an oxiranylmethylene group.

As regards these intermediates, the production thereof and their further processing, more details will be provided below. The radicals Z—X and R²O— may be on the other hand be attached in any desired combination at the positions 5 through 8 of the coumarin skeleton, the positions 6 and 7 being preferred.

The compounds of the general formula III may be produced by reacting a compound of the general formula VI, in which R², R³ and R⁴ have the above noted meanings, either with alkyl dihalides hal-X-hal, in which X denotes an alkylene group with 2 to 5 carbon atoms, or with halogenalcohols hal-X—OH, in which X denotes an alkylene group with 2 to 5 C atoms, firstly to produce compounds of the general formula VIII

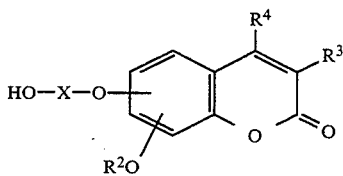

(VIII)

wherein X, $R^2$, $R^3$ and $R^4$ have the meanings given in conjunction with the general formula I, and finally with a sulfonic acid chloride in a conventional manner. The reactions with the said halogen compounds are as in the forms of the method (a) and (b) described in the above. Use is made of the bases, solvents, catalysts, reaction temperatures, protective atmospheres and pressure conditions as described therein. However preferably an alkali metal hydride, carbonate or hydrogencarbonate is utilized as a base and dimethylformamide or butanone(-2) as a solvent. The reaction temperature will preferably be between 60° C. and 100° C.

In the reaction of the compound of the general formula VIII with a sulfonic acid chloride the sulfonyl compounds of the general formula III are formed in a known manner with the above noted meanings for X, $R^2$, $R^3$ and $R^4$ and with alkylsulfonyloxy, trifluoromethylsulfonyloxy or with phenylsulfonyloxy optionally substituted with alkyl, nitro or halogen as the leaving group A. For this purpose the corresponding alcohol of the general formula VIII is reacted with an alkyl, trifluoromethyl or phenylsulfonic acid halide, optionally substituted with alkyl, nitro or halogen, and preferably methane- or p-toluenesulfonic acid chloride. In order to bind the hydrohalic acid formed such reactions are performed in the presence of a base as for instance of an alkali metal or alkaline earth metal carbonate or hydrogencarbonate or of a tertiary or aromatic amine, in which respect use is preferably made of tertiary amines such as triethylamine. The reactions are best performed in the presence of solvents which are inert with respect to the reactants. Well suited for this purpose are aromatic solvents such as toluene, xylene or the like or dipolar aprotic solvents such as aliphatic or cycloaliphatic ethers, carboxylic acid dialkylamides, tetraalkylureas, ketones, sulfoxides and halogenated alkanes. It is preferred to use halogenated alkanes such as chloroform or dichloromethane. The reaction temperature may be between −30° C. and +60° C., preferably between 0° C. and +30° C. To avoid oxidative by-products a protective gas atmosphere, for instance nitrogen or argon is used.

The compounds of the general formula IV may be produced in the same manner as the compounds of the general formula III by reacting a compound of the general formula VI, in which $R^2$, $R^3$ and $R^4$ have the above noted meanings, with epichlorohydrin or epibromohydrin, the same reaction conditions being applied as in the forms (a) and (b) of the method.

The compounds of the general formula IX

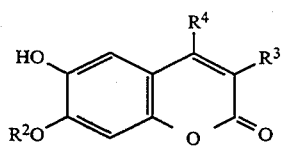

(IX)

wherein $R^2$, $R^3$ and $R^4$ have the above noted meanings, $R^4$ however not having the meaning of hydrogen, may be produced by reacting a 2-alkoxyhydroquinone $R^2O$— $C_6H_3(OH)_2$ with a β-ketocarboxylic acid ester of the general formula X,

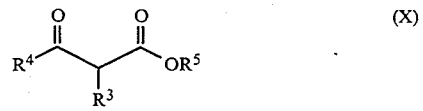

(X)

wherein $R^3$ and $R^4$ have the above noted meanings and $R^5$ denotes a lower alkyl radical, in a per se known manner in the presence of an acidic catalyst. The acidic catalyst may be a mineral or Lewis acid without a solvent or with solvents which are inert with respect to the reaction, such as for instance alcohols or glacial acetic acid, and preferably 50 to 100% sulfuric acid without any further solvent. The reaction is performed at 0° C. to 60° C., and preferably at 0° C. to 25° C.

It is surprising that this reaction proceeds regioselectively. The other conceivable reaction products, 5-alkoxy-6-hydroxy- and 8-alkoxy-6-hydroxy-coumarin derivatives, were not found in any single case.

The intermediates which are utilized for the synthesis of the compounds of the general formula I and have the general formulas III, IV, VI, VIII and IX with the above noted meanings for A, X, $R^2$, $R^3$ and $R^4$ are novel with a few exceptions. The new intermediates, more particularly those of the general formula IX, are therefore also claimed as part of the present invention. However on the other hand known compounds of the general formula XI are disclaimed in which Z—X jointly denote a hydrogen atom and simultaneously either $R^3$ is H and $R^4$ is H, methyl or phenyl or $R^3$ is methyl and $R^4$ is H, and furthermore 7-methoxy-6-(oxiranylmethoxy)-2H-1-benzopyran-2-one and 7-methoxy-4-methyl-6-(oxiranylmethoxy)-2H-1-benzopyran-2-one.

If they contain one or more centers of asymmetry the compounds in accordance with the invention may exist in the form of racemates, enantiomers or diastereomers. Each of the these forms is claimed as part of the present invention either per se or in admixture with one or more other forms.

Furthermore the present invention relates to medicaments which as an active principle contain one or a plurality of the compounds in accordance with the invention of the general formula I and optionally additionally inert adjuvants such as for instance water, vegetable oils, polyethylene glycols, glycerol esters, gelatine, carbohydrates such as lactose or starch, magnesium stearate, talcum, Vaseline ®, preservatives, wetting agents, emulsifiers, physiologically compatible salts, buffer substances, dyes, flavorants and aroma improving substances. The selection of such additives will be dependent on the desired form of administration such as for instance tablets, dragees, juices, ampoules, suppositories, ointments or sprays. The compounds in accordance with the invention may be furthermore administered in conjunction with other known active principles.

In the following the compounds in accordance with the invention, the methods for producing the same and the results of pharmacological investigations thereon will be described in more detail.

I Examples 1 through 66 for Final Products of the General Formula I

For the production of the compounds described in more detail in the following examples 1 through 66 the following methods were utilized:

Method A:

5 to 10 g of the methanesulfonyloxyalkoxy-2H-1-benzopyran-2-one or halogenalkoxy-2H-1-benzopyran-2-one correspondingly substituted with $R^2O$, $R^3$ and $R^4$ are agitated in a nitrogen atmosphere with 1.0 to 1.5 equivalents of the desired $R^1$-substituted piperidine or piperazine in the form of the base or of the hydrochloride, with 2.0 equivalents of potassium carbonate and with approximately 1 g of potassium iodide in approximately 200 ml of dimethylformamide for 4 to 60 h at 40° C. to 80° C. The solvent is removed under vacuum, the residue is taken up in chloroform or ethyl acetate, washed optionally with dilute caustic soda solution and then with water, dried over sodium sulfate and the solvent removed again. Purification is by recrystallization or by column chromatography on silica.

Method B:

4 to 11 g of the methanesulfonyloxyalkoxy-2H-1-benzopyran-2-one or halogenalkoxy-2H-1-benzopyran-2-one correspondingly substituted with $R^2O$, $R^3$ and $R^4$ are agitated in a nitrogen atmosphere with one equivalent of the desired $R^1$ substituted piperidine or piperazine in the form of the base or of the hydrochloride, with 2.0 equivalents of potassium hydrogencarbonate and with approximately 1 g of potassium iodide in approximately 200 ml of dimethylformamide for 4 to 75 h at 25° C. to 90° C. The solvent is removed under vacuum, the residue is taken up in chloroform or ethyl acetate, washed optionally with dilute sodium hydroxide solution and then with water, dried over sodium sulfate and the solvent removed again. Purification is by recrystallization or by column chromatography on silica gel.

Method C:

5.0 g of the oxiranylmethoxy-2H-1-benzopyran-2-one correspondingly substituted with $R^2O$, $R^3$ and $R^4$ are agitated in a nitrogen atmosphere with one equivalent of the desired $R^1$-substituted piperidine or piperazine in 250 ml of ethanol for 1 to 7 days in a nitrogen atmosphere at 25° C. to 50° C. The solvent is removed in vacuum and purification is performed by recrystallization or by column chromatography on silica gel.

Method D:

One equivalent of hydroxy-2H-1-benzopyran-2-one correspondingly substituted with $R^2O$, $R^3$ and $R^4$ in dimethylformamide is added dropwise under nitrogen to 1.05 to 1.1 equivalents of sodium hydride in dimethylformamide and agitation is performed for two hours at room temperature. Then 1.1 equivalents of the desired $R^1$-substituted 1-(3-chloropropyl)piperidine or -piperazine and approximately 0.2 equivalents of potassium iodide are added thereto and agitation performed for 2.5 to 5 hours in nitrogen at 85° C. to 90° C. The solvent is removed under vacuum, recrystallization is performed or the residue taken up in chloroform, if necessary washing is performed with dilute sodium hydroxide and then with water followed by drying over sodium sulfate. The next step is for the solvent to be again removed and then purification is performed by recrystallization.

Method E:

1 to 2 equivalents fumaric acid dissolved in ethanol, isopropanol or acetone are added to a solution of the base in chloroform, ethanol, isopropanol, acetone or chloroform/diethylether. The fumarate precipitates in crystalline form at once or upon evaporating and is recrystallized.

Method F:

Hydrogen chloride gas is fed into a solution of the base in diethylether and/or chloroform up to a complete precipitation of the hydrochloride. The precipitate thus obtained is vacuum filtered and recrystallized.

Method G:

Approximately 1.5 equivalents of HCl (6 molar in isopropanol) are added to a solution of the base in isopropanol, chloroform or chloroform and diethyl ether. The resulting precipitate is vacuum filtered and recrystallized.

In the case of the methods E through G, unless otherwise indicated in the examples, 1.0 HCl or $C_4H_4O_4$ is added to form the respective acid addition compound.

Example 1

7-methoxy-6-[3-(4-phenyl-1-piperazinyl)propoxy]-2H-1-benzopyran-2-one.

Method A (23 h at 60° C.); starting materials: 6-[3-(methanesulfonyloxy)propoxy]-7-methoxy-2H-1-benzopyran-2-one (see example 67) and 1-phenylpiperazine; yield 55%; fusion point 124° to 125° C. (from ethanol). Fumarate: method E; yield 88%; fusion point 172° to 173° C. (from ethanol).

Example 2

6-methoxy-7-[3-(4-phenyl-1-piperazinyl)propoxy]-2H-1-benzopyran-2-one.

Method B (9 h at 70° C.); starting materials: 7-[3-(chloropropoxy)-6-methoxy-2H-1-benzopyran-2-one (see example 69) and 1-phenylpiperazine; yield 94%; fusion point 82° to 83° (from isopropanol and TBME). Fumarate: method E; yield 94%; fusion point 168° to 170° C. (from isopropanol and TBME).

Example 3

7-ethoxy-6-[3-(4-phenyl-1-piperazinyl)propoxy]-2H-1-benzopyran-2-one.

Method A (26 h at 60° C.); starting materials: 6-(3-chloropropoxy)-7-ethoxy-2H-1-benzopyran-2-one (see example 70) and 1-phenylpiperazine; yield 57%; fusion point 151° to 153° (from methanol and ethanol). Fumarate: method E; yield 78%; fusion point 170° to 173° C. (from ethanol).

Example 4

6-ethoxy-7-[3-(4-phenyl-1-piperazinyl)propoxy]-2H-1-benzopyran-2-one.

Method B (40 h at 50° C.); starting materials: 6-ethoxy-7-[3-(methanesulfonyloxy)-propoxy]-2H-1-benzopyran-2-one (see example 71) and 1-phenylpiperazine; yield 76%; fusion point 116° to 117° C. (from isopropanol). Fumarate: method E; yield 94%; fusion point 185° to 187° C. (from ethanol and acetone).

Example 5

6-(cyclopentyloxy)-7-[3-(4-phenyl-1-piperazinyl)propoxy]-2H-1-benzopyran-2-one.

Method B (25 h at 40° C.); starting materials: 6-(cyclo-pentyloxy)-7-[3-(methanesulfonyloxy)propoxy]-2H-1-benzopyran-2-one (example 72) and 1-phenylpiperazine; yield 68%; fusion point 101°–103° C. (from TBME and isopropanol). Fumarate: method E; yield 88%; fusion point 171°–173° C. (from acetone).

Example 6

7-methoxy-6-{3-[4-(3-trifluoromethylphenyl)-1-piperazinyl]propoxy}-2H-1-benzopyran-2-one.

Method A (10 h at 80° C.); starting materials: 6-[3-(methanesulfonyloxy)propoxy]-7-methoxy-2H-1-benzopyran-2-one (example 67) and 1-(3-trifluoromethylphenyl)-piperazine; yield 71% oil. Hydrochloride: method F; yield 87%; fusion point 120°–122° C. (from ethanol).

Example 7

7-ethoxy-6-{3-[4-(2-methoxyphenyl)-1-piperazinyl]-propoxy}-2H-1-benzopyran-2-one.

Method A (48 h at 60° C.); starting materials: 6-(3-chloropropoxy)-7-ethoxy-2H-1-benzopyran-2-one (example 70) and 1(2-methoxyphenyl)piperazine hydrochloride; yield 49%; fusion point 78°–80° C. (from isopropanol). Fumarate: method E; yield 82%; fusion point 149°–150° C. (from ethanol).

Example 8

7-{3-[4-(bis(4-fluorophenyl)methyl)-1-piperazinyl]-propoxy}-6-methoxy-2H-1-benzopyran-2-one.

Method B (36 h at 60° C.); starting materials: 7-[3-(methanesulfonyloxy)propoxy]-6-methoxy-2H-1-benzopyran-2-one (example 68) and 1-[bis(4-fluorophenyl)methyl]-piperazine; yield 76% Öl. Fumarate: method E; yield 82%; fusion point 200°–202° C. (from acetone).

Example 9

7-methoxy-6-[3-(4-phenyl-1-piperidinyl)propoxy]-2H-1-benzopyran-2-one.

Method A (4 h at 80° C.); starting materials: 6-[3-methanesulfonyloxy)propoxy]-7-methoxy-2H-1-benzopyran-2-one (example 67) and 4-phenylpiperidine; yield 55%; fusion point 123°–125° C. (from isopropanol). Hydrochloride: method G; yield 96%; fusion point 212°–215° C. (from isopropanol and ethanol).

Example 10

6-methoxy-7-[3-(4-phenyl-1-piperidinyl)propoxy]-2H-1-benzopyran-2-one.

Method B (20 h at 60° C.); starting materials: 7-[3-(methanesulfonyloxy)propoxy]-6-methoxy-2H-1-benzopyran-2-one (example 68) and 4-phenylpiperidine; yield 73%; fusion point 97°–99° C. (from isopropanol). Hydrochloride: method G; yield 93%; fusion point 198°–200° C. (from isopropanol).

Example 11

6-ethoxy-7-[3-(4-phenyl-1-piperidinyl)propoxy]-2H-1-benzopyran-2-one.

Method B (40 h at 50° C.); starting materials: 6-ethoxy-7-[3-(methanesulfonyloxypropoxy]-2H-1-benzopyran-2-one (example 71) and 4-phenylpiperidine; yield 81%; fusion point 77°–79° C. (from TBME and isopropanol). Fumarate: method E; yield 74%; fusion point 212°–215° C. (from ethanol and acetone).

Example 12

6-(1-methylethoxy)-7-[3-(4-phenyl-1-piperidinyl)-propoxy]-2H-1-benzopyran-2-one.

Method B (24 h at 60° C.); starting materials: 7-[3-(methanesulfonyloxy)propoxy]-6-(1-methylethoxy)-2H-1-benzopyran-2-one (example 73) and 4-phenylpiperidine; yield 69%; fusion point 86°–87° C. (from TBME). Fumarate: method E; yield 90%; fusion point 164°–167° C. (from ethanol and acetone).

Example 13

6-(cyclopentyloxy)-7-[3-(4-phenyl-1-piperidinyl)-propoxy]-2H-1-benzopyran-2-one.

Method B (30 h at 45° C.); starting materials: 6-(cyclo-pentyloxy)-7-[3-(methanesulfonyloxy)propoxy]-2H-1-benzopyran-2-one (example 72) and 4-phenylpiperidine; yield 48%; fusion point 96°–97° C. (from TBME and isopropanol). Fumarate: method E; yield 83%; fusion point 171°–173° C. (from acetone).

Example 14

7-{3-[4-(bis(4-fluorophenyl)hydroxymethyl)-1-piperidinyl]propoxy}-6-methoxy-2H-1-benzopyran-2-one.

Method B (36 h at 60° C.); starting materials: 7-[3-(methanesulfonyloxy)propoxy]-6-methoxy-2H-1-benzopyran-2-one (example 68) and 4-[bis(4-fluorophenyl)hydroxymethyl]piperidine; yield 46% oil. Fumarate ($\times 0.5$ $C_4H_4O_4$): method E; yield 60%; fusion point 140°–142° C. (from acetone and petroleum ether).

Example 15

6-{3-[4-(bis(4-fluorophenyl)methylene)-1-piperidinyl]-propoxy}-7-methoxy-2H-1-benzopyran-2-one.

Method A (6 h at 80° C.); starting materials: 6-[3-methanesulfonyloxy)propoxy]-7-methoxy-2H-1-benzopyran-2-one. (example 67) and 4-[bis-(4-fluorophenyl)-hydroxymethyl]piperidine; yield 64% oil. Heating in alcoholic hydrochloric acid leads to the desired compound with the splitting off of water. Fumarate: method E; yield 79%; fusion point 135°–138° C. (from ethanol and petroleum ether).

Example 16

6-{3-[4-(diphenylmethyl)-1-piperidinyl]propoxy}-7-methoxy-2H-1-benzopyran-2-one.

Method B (6 h at 80° C.); starting materials: 6-[3-(methanesulfonyloxy)propoxy]-7-methoxy-2H-1-benzopyran-2-one (example 67) and 4-(diphenylmethyl)piperidine; yield 75% oil. Fumarate: method E; yield 73%; fusion point 199°–200° C. (from acetone and methanol).

Example 17

7-{3-[4-(diphenylhydroxymethyl)-1-piperidinyl]-propoxy}-6-methoxy-2H-1-benzopyran-2-one.

Method B (12 h at 70° C.); starting materials: 7-(3-chloropropoxy)-6-methoxy-2H-1-benzopyran-2-one (example 69) and 4-(diphenylhydroxymethyl)piperidine; yield 54% oil. Fumarate: method E; yield 82%; fusion point 155°–157° C. (from ethanol and water).

Example 18

($\pm$)-7-methoxy-6-[2-hydroxy-3-(4-phenyl-1-piperazinyl)propoxy]-2H-1-benzopyran-2-one. Method C (5 d at 40° C.); starting materials: 7-methoxy-6-(oxiranylmethoxy)-2H-1-benzopyran-2-one and 1-phenylpiperazine; yield 99%; fusion point 160°–162° C. (from isopropanol and ethanol). Hydrochloride: method F; yield 78%; fusion point 222°–225° C. (from isopropanol, ethanol and methanol).

Example 19

($\pm$)-6-{3-[4-(3-chlorophenyl)-1-piperazinyl]-2-hydroxypropoxy}-7-methoxy-2H-1-benzopyran-2-one.

Method C (3 d at 40° C.); starting materials: 7-methoxy-6-(oxiranylmethoxy)-2H-1-benzopyran-2-one and 1-(3-chlorophenyl)-piperazine; yield 85%; fusion point 140°–141° C. (from isopropanol). Hydrochloride (×1.7 HCl): method F; yield 88%; fusion point 222°–224° C.

Example 20

(±)-6-{2-hydroxy-3-[4-(3-trifluoromethylphenyl)-1-piperazinyl]propoxy}-7-methoxy-2H-1-benzopyran-2-one.

Method C (7 d at 25° C.); starting materials: 7-methoxy-6-(oxiranylmethoxy)-2H-1-benzopyran-2-one and 1-(3-trifluoromethylphenyl)piperazine; reacted in the raw condition to give the hydrochloride. Hydrochloride: method F; yield 30% (related to oxirane); fusion point 196°–197° C. (from isopropanol).

Example 21

(±)-7-{2-hydroxy-3-[4-(3-trifluoromethylphenyl)-1-piperazinyl]propoxy}-6-methoxy-2H-1-benzopyran-2-one.

Method C (1.5 d at 45° C.); starting materials: 6-methoxy-7-(oxiranylmethoxy)-2H-1-benzopyran-2-one (example 86) and 1-(3-trifluoromethylphenyl)piperazine; yield 80%; fusion point 133°–135° C. (from methanol). Hydrochloride: method F; yield 83%; fusion point 125°–128° C. (decomposes; from isopropanol).

Example 22

(±)-6-[2-hydroxy-3-(4-phenyl-1-piperidinyl)-propoxy]-7-methoxy-2H-1-benzopyran-2-one.

Method C (1 d at 50° C.); starting materials: 7-methoxy-6-(oxiranylmethoxy)-2H-1-benzopyran-2one and 4-phenylpiperidine; yield 88% oil. Hydrochloride: method F; yield 50%; fusion point 213°–216° C. (from isopropanol and ethanol).

Example 23

(±)-7-[2-hydroxy-3-(4-phenyl-1-piperidinyl)-propoxy]-6-methoxy-2H-1-benzopyran-2-one.

Method C (27 h at 45° C.); starting materials; 6-methoxy-7-(oxiranylmethoxy)-2H-1-benzopyran-2-one (example 86) and 4-phenylpiperidine; yield 69%; fusion point 114°–115° C. (from isopropanol and ethanol). Hydrochloride: method G; yield 82%; fusion point 202°–205° C. (from isopropanol and ethanol).

Example 24

(±)-6-[2-hydroxy-3-(4-hydroxy-4-phenyl-1-piperidinyl)propoxy]-7-methoxy-2H-1-benzopyran-2-one.

Method C (3 d at 40° C.); starting materials: 7-methoxy-6-(oxiranylmethoxy)-2H-1-benzopyran-2-one and 4-hydroxy-4-phenylpiperidine; yield 69%; fusion point 155°–157° C. (from isopropanol). Hydrochloride: method G; yield 88%; fusion point 202°–203° C. (from isopropanol).

Example 25

(±)-6-{3-[4-(bis(4-fluorophenyl)hydroxymethyl]-1-piperidinyl]-2-hydroxypropoxy}-7-methoxy-2H-1-benzopyran-2-one.

Method C (5 d at 45° C.); starting materials: 7-methoxy-6-(oxiranylmethoxy)-2H-1-benzopyran-2-one and 4-[bis(4-fluorophenyl)hydroxymethyl]piperidine; yield 45%; fusion point 220°–221° C. (from methanol and chloroform). Hydrochloride: method G; yield 99%; fusion point 172°–174° C. (from isopropanol and ethanol).

Example 26

7-methoxy-4-methyl-6-[3-(4-phenyl-1-piperazinyl)-propoxy]-2H-1-benzopyran-2-one.

Method B (32 h at 50° C.); starting materials: 6-[3-(methanesulfonyloxy)propoxy]-7-methoxy-4-methyl-2H-1-benzopyran-2-one (example 74) and 1-phenylpiperazine; yield 77%; fusion point 137°–140° C. (from isopropanol and ethanol). Fumarate: method E; yield 79%; fusion point 195°–200° C. (from ethanol and acetone).

Example 27

7-methoxy-4-methyl-6-[3-(4-phenyl-1-piperidinyl)-propoxy]-2H-1-benzopyran-2-one.

Method B (26 h at 50° C.); starting materials: 6-[3-(methanesulfonyloxy)propoxy]-7-methoxy-4-methyl-2H-1-benzopyran-2-one (example 74) and 4-phenylpiperidine; yield 77%; fusion point 141°–143° C. (from isopropanol and ethanol). Fumarate: method E; yield 89%; fusion point 221°–223° C. (from ethanol).

Example 28

7-methoxy-3,4-dimethyl-6-[3-(4-phenyl-1-piperazinyl)-propoxy]-2H-1-benzopyran-2-one.

Method A (45 h at 50° C.); starting materials: 6-[3-(methanesulfonyloxy)propoxy]-7-methoxy-3,4-dimethyl-2H-1-benzopyran-2-one (example 75) and 1-phenylpiperazine; yield 64%; fusion point 151°–152° C. (from ethanol and methanol). Fumarate (×0.5 $C_4H_4O_4$): method E; yield 92%; fusion point 207°–209° C. (from ethanol and methanol).

Example 29

7-methoxy-3,4-dimethyl-6-[3-(4-phenyl-1-piperidinyl)-propoxy]-2H-1-benzopyran-2-one.

Method A (9 h at 60° C.); starting materials: 6-[3-(methanesulfonyloxy)propoxy]-7-methoxy-3,4-dimethyl-2H-1-benzopyran-2-one (example 75) and 4-phenylpiperidine; yield 64%; fusion point 152°–153° C. (from ethanol and isopropanol). Fumarate (×0.5 $C_4H_4O_4$): method E; yield 92%; fusion point 209°–210° C. (from ethanol and methanol).

Example 30

6-{3-[4-(4-chlorophenylmethyl)-1-piperazinyl]-propoxy}-7-methoxy-3,4-dimethyl-2H-1-benzopyran-2-one.

Method D (5 h at 90° C.); starting materials: 6-hydroxy-7-methoxy-3,4-dimethyl-2H-1-benzopyran-2-one (example 103) and 1-[(4-chlorophenyl)methyl]-4-(3-chloropropyl)piperazine; yield: 74%; fusion point 96°–97° C. (from isopropanol and petroleum ether). Hydrochloride (x 2 HCl): method G; yield 95%; fusion point 255°–260° C. (from isopropanol and water).

Example 31

7-methoxy-6-[3-(4-phenyl-1-piperazinyl)propoxy[-4-(trifluoromethyl)-2H-1-benzopyran-2-one.

Method D (3 h at 85° C.); starting materials: 6-hydroxy-7-methoxy-4-(trifluoromethyl)-2H-1-benzopyran-2-one (example 104) and 1-(3-chloropropyl)-4-phenylpiperazine; yield 37%; the fusion point being 115° to 116° C. (from isopropanol). Fumarate: method E; yield 70%; fusion point 183°–185° C. (from ethanol and isopropanol).

Example 32

7-methoxy-6-[3-(4-phenyl-1-piperidinyl)propoxy]-4-(trifluoromethyl)-2H-1-benzopyran-2-one.

Method D (3 h at 85° C.); starting materials: 6-hydroxy-7-methoxy-4-(trifluoromethyl)-2H-1-benzopyran-2-one (example 104) and 1-(3-chloropropyl)-4-phenylpiperidine; yield 45%; fusion point 125°–126° C. (from TBME and methanol). Fumarate: method E; yield 59%; fusion point 176°–179° C. (from ethanol and TBME).

Example 33

7-methoxy-6-[3-phenyl-1-piperazinyl)propoxy]-4-propyl-2H-1-benzopyran-2-one.

Method A (21 h at 60° C.); starting materials: 6-[3-(methanesulfonyloxy)propoxy]-7-methoxy-4-propyl-2H-1-benzopyran-2-one (example 76) and 1-phenylpiperazine; yield 55%; fusion point 108°–109° C. (from isopropanol and ethanol). Fumarate (x 1.2 $C_4H_4O_4$): method E; yield 79%; fusion point 206°–207° C. (from acetone and methanol).

Example 34

7-methoxy-6-[3-(4-phenyl-1-piperidinyl)propoxy]-4-propyl-2H-1-benzopyran-2-one.

Method A (20 h at 60° C.); starting materials: 6-[3-(methanesulfonyloxy)propoxy]-7-methoxy-4-propyl-2H-1-benzopyran-2-one (example 76) and 4-phenylpiperidine; yield 54%; fusion point 101°–102° C. (from TBME and petroleum ether). Fumarate: method E; yield 62%; fusion point 191°–194° C. (from acetone and methanol).

Example 35

7-methoxy-4-(1-methylethyl)-6-[3-(4-phenyl-1-piperazinyl)propoxy]-2H-1-benzopyran-2-one.

4.0 g (17 mmol) 6-hydroxy-7-methoxy-4-(1-methylethyl)-2H-1-benzopyran-2-one (example 105), 4.7 g (20.5 mmol) 1-(3-chloropropyl)-4-phenylpiperazine, 4.7 g (34 mmol) potassium carbonate and 1.0 g potassium iodide are agitated in 300 ml DMF for 44 h under nitrogen at 60° C. After filtration and removal of the solvent in vacuum, the residue is taken up in chloroform and washed with dilute sodium hydroxide solution and with water, dried over sodium sulfate and then evaporated again. Yield 5.5 g (74%) of crystals with a fusion point of 94°–96° C. (from isopropanol and TBME). Fumarate: method E; yield 88%; fusion point 175°–176° C. (from isopropanol and ethanol).

Example 36

7-methoxy-4-(1-methylethyl)-6-[3-(4-phenyl-1-piperidinyl)propoxy]-2H-1-benzopyran-2-one.

Method D (2.5 h at 85° C.); starting materials: 6-hydroxy-7-methoxy-4-(1-methylethyl)-2H-1-benzopyran-2-one (example 105) and 1-(3-chloropropyl)-4-phenyl-piperidine; yield 85%; fusion point 62°–65° C. (from TBME). Fumarate: method E; yield 65%; fusion point 155°–157° C. (from acetone, boiled out with TBME).

Example 37

3-butyl-7-methoxy-4-methyl-6-[3-(4-phenyl-1-piperazinyl)propoxy]-2H-1-benzopyran-2-one.

Method B (60 h at 50° C.); starting materials: 3-butyl-6-(3-chloropropoxy)-7-methoxy-4-methyl-2H-1-benzopyran-2-one (example 77) and 1-phenylpiperazine; yield 72%; fusion point 130°–131° C. (from isopropanol and TBME). Fumarate: method E; yield 57%; fusion point 205°–208° C. (from acetone and water).

Example 38

3-butyl-7-methoxy-4-methyl-6-[3-(4-phenyl-1-piperidinyl)propoxy]-2H-1-benzopyran-2-one.

Method B (60 h at 50° C.); starting materials: 3-butyl-6-(3-chloropropoxy)-7-methoxy-4-methyl-2H-1-benzopyran-2-one (example 77) and 4-phenylpiperidine; yield 51% oily raw product. Fumarate: method E; yield 89%; fusion point 176°–178° C. (from acetone).

Example 39

7-methoxy-4-phenyl-6-[3-(4-phenyl-1-piperazinyl)propoxy]-2H-1-benzopyran-2-one.

Method B (60 h at 60° C.); starting materials: 6-[3-(methanesulfonyloxy)propoxy]-7-methoxy-4-phenyl-2H-1-benzopyran-2-one (example 78) and 1-phenylpiperazine; yield 86%; fusion point 139°–141° C. (from TBME and isopropanol). Fumarate: method E; yield 93%; fusion point 145°–147° C. (from acetone and diethylether).

Example 40

7-methoxy-4-phenyl-6-[3-(4-phenyl-1-piperidinyl)propoxy]-2H-1-benzopyran-2-one.

Method B (16 h at 60° C.); starting materials: 6-[3-methanesulfonyloxy)propoxy]-7-methoxy-4-phenyl-2H-1-benzopyran-2-one (example 78) and 4-phenylpiperidine; yield 100% oil. Fumarate: method E; yield 84%; fusion point 150°–152° C. (from acetone).

Example 41

7-methoxy-4-methyl-3-phenyl-6-[3-(4-phenyl-1-piperazinyl)propoxy]-2H-1-benzopyran-2-one.

Method B (40 h at 50° C.); starting materials: 6-(3-chloropropoxy)-7-methoxy-4-methyl-3-phenyl-2H-1-benzopyran-2-one (example 79) and 1-phenylpiperazine; yield 66%; fusion point 168°–170° C. (from isopropanol). Fumarate: method E; yield 95%; fusion point 219°–221° C. (from acetone).

Example 42

7,8,9,10-tetrahydro-3-methoxy-2-[3-(4-phenyl-1-piperazinyl)propoxy]-6H-dibenzo[b,d]pyran-6-one.

Method B (24 h at 60° C.); starting materials: 7,8,9,10-tetrahydro-2-[3-(methanesulfonyloxy)propoxy]-3-methoxy-6H-dibenzo[b,d]pyran-6-one (example 80) and 1-phenylpiperazine; yield 94%; fusion point 104°–106° C. (from TBME and isopropanol). Fumarate: method E; yield 92%; fusion point 160°–161° C. (from ethanol and acetone).

Example 43

7,8,9,10-tetrahydro-3-methoxy-2-[3-(4-phenyl-1-piperidinyl)propoxy]-6H-dibenzo[b,d]pyran-6-one.

Method B (20 h at 50° C.); starting materials: 7,8,9,10-tetrahydro-2-[3-(methanesulfonyloxy)propoxy]-3-methoxy-6H-dibenzo[b,d]pyran-6-one (example 80) and 4-phenylpiperidine; yield 100% (raw). Fumarate: method E; yield 72% on the basis of the methanesulfonyl compound; fusion point 184°–186° C. (from ethanol and acetone).

Example 44

2,3-dihydro-7-methoxy-8-[2-(4-phenyl-1-piperazinyl)ethoxy]cyclopenta[c][1]benzopyran-4(1H)-one.

Method B (24 h at 80° C.); starting materials: 2,3-dihydro-8-[2-(methanesulfonyloxy)ethoxy]-7-methoxy-cyclopenta[c][1]-benzopyran-4(1H)-one (example 81) and 1-phenylpiperazine; yield 90%; fusion point 155°–156° C. (from isopropanol). Fumarate: method E; yield 94%; fusion point 182°–185° C. (from acetone).

Example 45

2,3-dihydro-7-methoxy-8-[3-(4-phenyl-1-piperazinyl)-propoxy]cyclopenta[c][1]benzopyran-4(1H)-one.

Method B (40 h at 50° C.); starting materials: 2,3-dihydro-8-[3-(methanesulfonyloxy)propoxy]-7-methoxy-cyclopenta[c][1]-benzopyran-4(1H)-one (example 82) and 1-phenylpiperazine; yield >100% oily raw product. Fumarate: method E; yield 72% related to the methanesulfonyl compound; fusion point 184°–186° C. (from ethanol and acetone).

Example 46

2,3-dihydro-7-methoxy-8-[4-(4-phenyl-1-piperazinyl)-butyloxy]cyclopenta[c][1]benzopyran-4(1H)-one.

Method B (16 h at 80° C.); starting materials: 2,3-dihydro-8-[4-(methanesulfonyloxy)butyloxy]-7-methoxy-cyclopenta[c][1]-benzopyran-4(1H)-one (example 84) and 1-phenylpiperazine; yield 55%; fusion point 162°–165° C. (from ethanol). Fumarate: method E; yield 95%; fusion point 179°–183° C. (from acetone).

Example 47

2,3-dihydro-7-methoxy-8-[5-(4-phenyl-1-piperazinyl)-pentyloxy]cyclopenta[c][1]benzopyran-4(1H)-one.

Method B (10 h at 80° C.); starting materials: 8-(5-bromopentyloxy)-2,3-dihydro-7-methoxycyclopenta[c][1]benzopyran-4(1H)-one (example 85) and 1-phenylpiperazine; yield 97%; fusion point 118°–120° C. (from isopropanol). Fumarate (x 0.5 $C_4H_4O_4$): method E; yield 93%; fusion point 153°–155° C. (from isopropanol and TBME).

Example 48

2,3-dihydro-7-methoxy-8-[2-(4-phenyl-1-piperidinyl)ethoxy]cyclopenta[c][1]benzopyran-4(1H)-one.

Method B (16 h at 60° C.); starting materials: 2,3-dihydro-8-[2-(methanesulfonyloxy)ethoxy]-7-methoxy-cyclopenta[c][1]-benzopyran-4(1H)-one (example 81) and 4-phenylpiperidine; yield 93%; fusion point 150°–152° C. (from isopropanol). Fumarate: method E; yield 84%; fusion point 185°–187° C. (from ethanol and isopropanol).

Example 49

2,3-dihydro-7-methoxy-8-[3-(4-phenyl-1-piperidinyl)-propoxy]cyclopenta[c][1]benzopyran-4(1H)-one.

Method B (60 h at 25° C.); starting materials: 2,3-dihydro-8-[3-(methanesulfonyloxy)propoxy]-7-methoxy-cyclopenta[c][1]-benzopyran-4(1H)-one (example 82) and 4-phenylpiperidine; yield 65%; fusion point 164°–166° C. (from isopropanol). Fumarate: method E; yield 86%; fusion point 195°–198° C. (from ethanol).

Example 50

2,3-dihydro-7-methoxy-8-[4-(4-phenyl-1-piperidinyl)-butyloxy]cyclopenta[c][1]benzopyran-4(1H)-one.

Method B (16 h at 60° C.); starting materials: 2,3-dihydro-8-[4-(methanesulfonyloxy)butyloxy]-7-methoxy-cyclopenta[c][1]-benzopyran-4(1H)-one (example 84) and 4-phenylpiperidine; yield 73%; fusion point 104°–105° C. (from TBME). Fumarate: method E; yield 77%; fusion point 192°–193° C. (from isopropanol).

Example 51

2,3-dihydro-7-methoxy-8-[5-(4-phenyl-1-piperidinyl)-pentyloxy]cyclopenta[c][1]benzopyran-4(1H)-one.

Method B (20 h at 80° C.); starting materials: 8-(5-bromopentyloxy)-2,3-dihydro-7-methoxy-cyclopenta[c][1]benzopyran-4(1H)-one (example 85) and 4-phenylpiperidine; yield 37%; fusion point 103°–105° C. (from isopropanol and TBME). Fumarate: method E; yield 94%; fusion point 176°–178° C. (from isopropanol and TBME).

Example 52

8-{3-[4-(4-fluorophenyl)-1-piperazinyl]propoxy}-2,3-dihydro-7-methoxy-cyclopenta[c][1]benzopyran-4(1H)-one.

Method B (12 h at 55° C.); starting materials: 2,3-dihydro-8-[3-(methanesulfonyloxy)propoxy]-7-methoxy-cyclopenta[c][1]-benzopyran-4(1H)-one (example 82) and 1-(4-fluorophenyl)piperazine; yield 84%; fusion point 139°–141° C. (from ethanol). Fumarate: method E; yield 90%; fusion point 195°–200° C. (from ethanol).

Example 53

8-{3-[4-(2,3-dimethylphenyl)-1-piperazinyl]propoxy}-2,3-dihydro-7-methoxy-cyclopenta[c][1]benzopyran-4(1H)-one.

Method B (20 h at 60° C.); starting materials: 2,3-dihydro-8-[3-(methanesulfonyloxy)propoxy]-7-methoxy-cyclopenta[c][1]-benzopyran-4(1H)-one (example 82) and 1-(2,3-dimethylphenyl)-piperazine; yield 84%; fusion point 164°–166° C. (from ethanol). Fumarate: method E; yield 94%; fusion point 235°–237° C. (from acetone).

Example 54

2,3-dihydro-7-methoxy-8-{3-[4-(2-methoxyphenyl)-1-piperazinyl]propoxy}cyclopenta[c][1]benzopyran-4(1H)-one.

Method A (40 h at 50° C.); starting materials: 8-(3-chloropropoxy)-2,3-dihydro-7-methoxy-cyclopenta[c][1]benzopyran-4(1H)-one (example 83) and 1-(2-methoxyphenyl)piperazine hydrochloride; yield 56%; fusion point 177°–178° C. (from chloroform and ethanol). Fumarate: method E; yield 87%; fusion point 173°–174° C. (from acetone).

Example 55

2,3-dihydro-7-methoxy-8-{3-[4-(3-methoxyphenyl)-1-piperazinyl]propoxy}cyclopenta[c][1]benzopyran-4(1H)-one.

Method B (60 h at 50° C.); starting materials: 8-(3-chloropropoxy)-2,3-dihydro-7-methoxy-cyclopenta[c][1]benzopyran-4(1H)-one (example 83) and 1-(3-methoxyphenyl)piperazine; yield 58%; fusion point 130°–132° C. (from ethanol and isopropanol). Fumarate: method E; yield 80%; fusion point 174°–175° C. (from acetone).

Example 56

2,3-dihydro-7-methoxy-8-{3-[4-(4-methoxyphenyl)-1-piperazinyl]propoxy}cyclopenta[c][1]benzopyran-4(1H)-one.

Method A (60 h at 40° C.); starting materials: 8-(3-chloropropoxy)-2,3-dihydro-7-methoxy-cyclopenta[c][1]benzopyran-4(1H)-one (example 83) and 1-(4-methoxyphenyl)piperazine dihydrochloride; yield 45%; fusion point 155°–156° C. (from ethanol). Fumarate: method E; yield 96%; fusion point 207°–210° C. (from acetone).

Example 57

8-{3-[4-(2-ethoxyphenyl)-1-piperazinyl]propoxy}-2,3-dihydro-7-methoxy-cyclopenta[c][1]benzopyran-4(1H)-one.

Method B (40 h at 50° C.); starting materials: 8-(3-chloropropoxy)-2,3-dihydro-7-methoxycyclopenta[c][1]benzopyran-4(1H)-one (example 83) and 1-(2-ethoxyphenyl)piperazine hydrochloride; yield 72%; fusion point 169°–170° C. (from isopropanol). Fumarate: method E; yield 85%; fusion point 159°–161° C. (from acetone).

Example 58

8-{3-[4-(2-chlorophenyl)-1-piperazinyl]propoxy}-2,3-dihydro-7-methoxy-cyclopenta[c][1]benzopyran-4(1H)-one.

Method B (70 h at 50° C.; 4 equivalents of potassium hydrogencarbonate); starting materials: 8-(3-chloropropoxy)-2,3-dihydro-7-methoxy-cyclopenta [c][1]benzopyran-4(1H)-one (example 83) and 1-(2-chlorophenyl)piperazine dihydrochloride; yield 61% raw product. Fumarate ($\times 0.5$ $C_4H_4O_4$): method E; yield 76%; fusion point 206°–209° C. (from acetone).

Example 59

2,3-dihydro-7-methoxy-8-{3-[4-(2-methylphenyl)-1-piperazinyl]propoxy}cyclopenta[c][1]benzopyran-4(1H)-one.

Method B (60 h at 45° C.; 4 equivalents of potassium hydrogencarbonate); starting materials: 8-(3-chloropropoxy)-2,3-dihydro-7-methoxycyclopenta[c][1]benzopyran-4(1H)-one (example 83) and 1-(2-methylphenyl)piperazine hydrochloride; yield 52% raw product. Fumarate: method E; yield 76%; fusion point 215°–218° C. (with decomposition; from chloroform and ethanol).

Example 60

2,3-dihydro-8-{3-[4-(2-hydroxyphenyl)-1-piperazinyl]propoxy}-7-methoxy-cyclopenta[c][1]benzopyran-4(1H)-one.

Method A (40 h at 50° C.; 4 equivalents of potassium carbonate); starting materials: 8-(3-chloropropoxy)-2,3-dihydro-7-methoxy-cyclopenta[c][1]benzopyran-4(1H)-one (example 83) and 1-(2-hydroxyphenyl)piperazine dihydrobromide; yield 54%; fusion point 136°–139° C. (from chloroform and ethanol). Fumarate: method E; yield 84%; fusion point 196°–199° C. (from acetone).

Example 61

2,3-dihydro-7-methoxy-8-{3-[4-(4-nitrophenyl)-1-piperazinyl]propoxy}cyclopenta[c][1]benzopyran-4(1H)-one.

Method B (60 h at 50° C.); starting materials: 8-(3-chloropropoxy)-2,3-dihydro-7-methoxy-cyclopenta[c][1]benzopyran-4(1H)-one (example 83) and 1-(4-nitrophenyl)piperazine; yield 43%; fusion point 226°–228° C. (decomposes; from acetone). Fumarate: method E; yield 92%; fusion point 216° C. (decomposes; from acetone).

Example 62

2,3-dihydro-7-methoxy-8-{3-[4-(2-pyridinyl)-1-piperazinyl]propoxy}cyclopenta[c][1]benzopyran-4(1H)-one.

Method B (75 h at 45° C.); starting materials: 8-(3-chloropropoxy)-2,3-dihydro-7-methoxy-cyclopenta[c][1]benzopyran-4(1H)-one (example 83) and 1-(2-pyridinyl)piperazine; yield 68%; fusion point 152°–154° C. (from chloroform and ethanol). Fumarate: method E; yield 96%; fusion point 205°–207° C. (from acetone).

Example 63

2,3-dihydro-7-methoxy-8-{3-[4-(2-pyrimidinyl)-1-piperazinyl]propoxy}cyclopenta[c][1]benzopyran-4(1H)-one.

Method B (60 h at 50° C.; 4 equivalents of potassium hydrogencarbonate); starting materials: 8-(3-chloropropoxy)-2,3-dihydro-7-methoxy-cyclopenta[c][1]benzopyran-4(1H)-one (example 83) and 1-(2-pyrimidinyl)piperazine dihydrochloride; yield 54%; fusion point 184°–186° C. (from chloroform and ethanol). Fumarate: method E; yield 77%; fusion point 226°–228° C. (from acetone).

Example 64

2,3-dihydro-7-methoxy-8-{3-[4-phenylmethyl)-1-piperidinyl]propoxy}cyclopenta[c][1]benzopyran-4(1H)-one.

Method B (25 h at 50° C.); starting materials: 2,3-dihydro-8-[3-(methanesulfonyloxy)propoxy]-7-methoxy-cyclopenta[c][1]-benzopyran-4(1H)-one (example 82) and 4-(phenylmethyl)piperidine; yield 71%; fusion point 119°–120° C. (from ethanol). Fumarate: method E; yield 91%; fusion point 195°–197° C. (from acetone).

Example 65

8-{3-[4-(bis(4-fluorophenyl)hydroxymethyl)-1-piperidinyl]propoxy}-2,3-dihydro-7-methoxy-cyclopenta[c][1]benzopyran-4(1H)-one.

Method B (38 h at 60° C.); starting materials: 8-(3-chloropropoxy)-2,3-dihydro-7-methoxy-cyclopenta[c][1]benzopyran-4(1H)-one (example 83) and 4-[bis(4-fluorophenyl)hydroxy-methyl]piperidine; yield 67%; fusion point 91° C. (decomposes; from acetone and TBME). Fumarate ($\times 0.5$ $C_4H_4O_4$): method E; yield 70%; fusion point 191° C. (decomposes; from water).

Example 66

8-{3-[4-(2-fluorophenyl)-1-piperazinyl]propoxy}-2,3-dihydro-7-methoxy-cyclopenta[c][1]benzopyran-4(1H)-one.

Method B (50 h at 60° C.); starting materials: 8-(3-chloropropoxy)-2,3-dihydro-7-methoxy-cyclopenta[c][1]benzopyran-4(1H)-one (example 83) and 1-(2-fluorophenyl)piperazine; yield 59%; fusion point 148°–150° C. (from ethanol). Fumarate ($\times H_2O$): method E; yield 78%; the fusion point being 205°–210° C. (from water).

II. Examples 67 to 85 of Intermediates of the General Formula III

For the production of the compounds described in following examples 67 through 85 the following procedures were utilized.

Method H:

The hydroxyalkoxy-2H-1-benzopyran-2-one correspondingly substituted with $R^2O$, $R^3$ and $R^4$ and 1.5 to 3 equivalents of triethylamine are mixed in chloroform at 0° to 25° C. dropwise with 1.5 to 3 equivalents of methanesulfonic acid chloride. Agitation for at least 30 min in nitrogen at 0° to 25° C. is followed by washing with water, drying over sodium sulfate, evaporation in a vacuum and purification by recrystallization.

Method I:

The hydroxy-2H-1-benzopyran-2-one correspondingly substituted with $R^2O$, $R^3$ and $R^4$, 1.25 to 1.5 equivalents of the desired α,ω-dihalogenalkane and 1.5 equivalents of potassium carbonate are agitated in 2-butanone under nitrogen for 16 to 60 h at 80° C. followed by filtration, removal of the solvent and purification, by recrystallization if possible. Optionally the product is dissolved in chloroform, washed with water, dried over sodium sulfate, evaporated in a vacuum and then purified by recrystallization.

Example 67

6-[3-(methanesulfonyloxy)propoxy]-7-methoxy-2H-1-benzopyran-2-one.

Method H; starting material: 6-(3-hydroxypropoxy)-7-methoxy-2H-1-benzopyran-2-one (example 87); yield 91%; fusion point 136°–137° C. (from methanol and ethanol).

Example 68

7-[3-(methanesulfonyloxy)propoxy]-6-methoxy-2H-1-benzopyran-2-one.

Method H; starting material: 7-(3-hydroxypropoxy)-6-methoxy-2H-1-benzopyran-2-one (example 88); yield 90%; fusion point 148°–149° C. (from isopropanol and ethanol).

Example 69

7-(3-chloropropoxy)-6-methoxy-2H-1-benzopyran-2-one.

Method I; starting materials: scopoletine and 1-bromo-3-chloropropane; yield 94%; fusion point 97°–98° C. (from ethanol and water).

Example 70

6-(3-chloropropoxy)-7-ethoxy-2H-1-benzopyran-2-one.

Method I; starting materials: 7-ethoxy-6-hydroxy-2H-1-benzopyran-2-one (example 100) and 1-bromo-3-chloropropane; yield 91%; fusion point 91°–92° C. (from ethanol and water).

Example 71

6-ethoxy-7-[3-(methanesulfonyloxy)propoxy]-2H-1-benzopyran-2-one.

Method H; starting material: 6-ethoxy-7-(3-hydroxypropoxy)-2H-1-benzopyran-2-one (example 89); yield 98%; fusion point 103°–105° C. (from ethanol).

Example 72

6-(cyclopentyloxy)-7-[3-(methanesulfonyloxy)propoxy]-2H-1-benzopyran-2-one.

Method H; starting material: 6-(cyclopentyloxy)-7-(3-hydroxypropoxy)-2H-1-benzopyran-2-one (example 90); yield>100% oily raw product.

Example 73

7-[3-(methanesulfonyloxy)propoxy]-6-(1-methylethoxy)-2H-1-benzopyran-2-one.

Method H; starting material: 7-(3-hydroxypropoxy)-6-(1-methylethoxy)-2H-1-benzopyran-2-one (example 91); yield 78%; fusion point 91°–93° C. (from ethanol).

Example 74

6-[3-(methanesulfonyloxy)propoxy]-7-methoxy-4-methyl-2H-1-benzopyran-2-one.

Method H; starting material: 6-(3-hydroxypropoxy)-7-methoxy-4-methyl-2H-1-benzopyran-2-one (example 92); yield 94%; fusion point 158°–159° C. (from ethanol and acetone).

Example 75

6-[3-(methanesulfonyloxy)propoxy]-7-methoxy-3,4-dimethyl-2H-1-benzopyran-2-one.

Method H; starting material: 6-(3-hydroxypropoxy)-7-methoxy-3,4-dimethyl-2H-1-benzopyran-2-one (example 93); yield 85%; fusion point 163°–164° C. (from ethanol and methanol).

Example 76

6-[3-(methanesulfonyloxy)propoxy]-7-methoxy-4-propyl-2H-1-benzopyran-2-one.

Method H; starting material: 6-(3-hydroxypropoxy)-7-methoxy-4-propyl-2H-1-benzopyran-2-one (example 94); yield 92%; fusion point 129°–130° C. (from methanol and ethanol).

Example 77

3-butyl-6-(3-chloropropoxy)-7-methoxy-4-methyl-2H-1-benzopyran-2-one.

Method I; starting materials: 3-butyl-6-hydroxy-7-methoxy-4-methyl-2H-1-benzopyran-2-one (example 107) and 1-bromo-3-chloropropane; yield 99%; fusion point 106°–107° C. (from ethanol).

Example 78

6-[3-(methanesulfonyloxy)propoxy]-7-methoxy-4-phenyl-2H-1-benzopyran-2-one.

Method H; starting material: 6-(3-hydroxypropoxy)-7-methoxy-4-phenyl-2H-1-benzopyran-2-one (example 95); yield 98%; fusion point 108°–109° C. (from ethanol).

Example 79

6-(3-chloropropoxy)-7-methoxy-4-methyl-3-phenyl-2H-1-benzopyran-2-one.

Method I; starting materials: 6-hydroxy-7-methoxy-4-methyl-3-phenyl-2H-1-benzopyran-2-one (example 108) and 1-bromo-3-chloropropane; yield 99%; fusion point 159°–161° C. (from ethanol).

Example 80

7,8,9,10-tetrahydro-2-[3-(methanesulfonyloxy)propoxy]-3-methoxy-6H-dibenzo[b,d]pyran-6-one.

Method H; starting material: 7,8,9,10-tetrahydro-2-(3-hydroxypropoxy)-3-methoxy-6H-dibenzo[b,d]pyran-6-one (example 96); yield 87%; fusion point 139°–141° C. (from ethanol).

Example 81

2,3-dihydro-8-[2-(methanesulfonyloxy)ethoxy]-7-methoxy-cyclopenta[c][1]benzopyran-4(1H)-one.

Method H; starting material: 2,3-dihydro-8-(2-hydroxy-ethoxy)-7-methoxy-cyclopenta[c][1]benzopyran-4(1H)-one (example 97); yield 96%; fusion point 185°–190° C. (from ethanol).

Example 82

2,3-dihydro-8-[3-(methanesulfonyloxy)propoxy]-7-methoxy-cyclopenta[c][1]benzopyran-4(1H)-one.

Method H; starting material: 2,3-dihydro-8-(3-hydroxy-propoxy)-7-methoxy-cyclopenta[c][1]benzopyran-4(1H)-one. (example 98); yield 88%; fusion point 149°–150° C. (from ethanol).

Example 83

8-(3-chloropropoxy)-2,3-dihydro-7-methoxy-cyclopenta[c][1]benzopyran-4(1H)-one.

Method I; starting materials: 2,3-dihydro-8-hydroxy-7-methoxy-cyclopenta[c][1]benzopyran-4(1H)-one (example 109) and 1-bromo-3-chloropropane; yield 84%; fusion point 174°–176° C. (from ethanol).

Example 84

2,3-dihydro-8-[4-(methanesulfonyloxy)butyloxy]-7-methoxy-cyclopenta[c][1]benzopyran-4(1H)-one.

Method H; starting material: 2,3-dihydro-8-(4-hydroxybutyloxy)-7-methoxy-cyclopenta[c][1]benzopyran-4(1H)-one (example 99); yield 91%; fusion point 130°–132° C. (from ethanol).

Example 85

8-(5-bromopentyloxy)-2,3-dihydro-7-methoxy-cyclopenta[c][1]benzopyran-4(1H)-one.

Method I; starting materials: 2,3-dihydro-8-hydroxy-7-methoxy-cyclopenta[c][1]benzopyran-4(1H)-one (example 109) and 1,5-dibromopentane; yield 51%; fusion point 103°–104° C. (from TBME).

III. Example 86 of an Intermediate of the General Formula IV

Example 86

(±)-6-methoxy-7-(oxiranylmethoxy)-2H-1-benzopyran-2-one.

25.0 g (130 mmol) of scopoletine, 15.3 ml (196 mmol) epichlorohydrin, 36.0 g (260 mmol) potassium carbonate and 2.5 g of potassium iodide are agitated in 500 ml DMF under nitrogen for 3 h at 80° C. After vacuum evaporation and repeated extraction with hot ethanol re-evaporation was performed. 21.2 g (66%); fusion point 143°–145° C. (from ethanol).

IV. Examples 87 to 99 of Intermediates of the General Formula XI with Z=OH

For the production of the compounds described in following examples 87 through 99 the procedures were as follows:

Method J:

The hydroxy-2H-1-benzopyran-2-one correspondingly substituted with $R^2O$, $R^3$ and $R^4$, 2 to 3 equivalents of the desired ω-halogenalkanol, 2.5 to 3 equivalents of potassium carbonate and 0.1 to 0.2 equivalents of potassium iodide are agitated in DMF for 16 to 45 h at 60° to 90° C., this step being followed by filtration, evaporation in a vacuum, dissolution in chloroform, washing with water, drying over sodium sulfate and evaporation.

Method K:

The hydroxy-2H-1-benzopyran-2-one correspondingly substituted with $R^2O$, $R^3$ and $R^4$, dissolved in DMF, is added dropwise at 25° C. under nitrogen into a suspension of 1.1 equivalents of sodium hydride in DMF. Agitation is performed for at least 30 min. 1.5 to 2 equivalents of the desired ω-halogenalcanol and 0.1 to 0.2 equivalents of potassium iodide are added. Agitation for 7 to 40 h at 80° to 90° C. is followed by evaporation in vacuum, dissolution in chloroform, washing with water, drying over sodium sulfate and evaporation.

Example 87

6-(3-hydroxypropoxy)-7-methoxy-2H-1-benzopyran-2-one.

Method J; starting materials: isoscopoletine and 3-chloro-1-propanol; yield 69%; fusion point 126°–127° C. (from TBME and isopropanol).

Example 88

7-(3-hydroxypropoxy)-6-methoxy-2H-1-benzopyran-2-one.

Method J; starting materials: scopoletine and 3-chloro-1-propanol; yield 65%; fusion point 107°–110° C. (from TBME).

Example 89

6-ethoxy-7-(3-hydroxypropoxy)-2H-1-benzopyran-2-one. Method K; starting materials: 6-ethoxy-7-hydroxy-2H-1-benzopyran-2-one and 3-chloro-1-propanol; yield 69%; fusion point 96°–98° C. (from isopropanol and TBME).

Example 90

6-(cyclopentyloxy)-7-(3-hydroxypropoxy)-2H-1-benzopyran-2-one.

Method K; starting materials: 6-(cyclopentyloxy)-7-hydroxy-2H-1-benzopyran-2-one (example 101) and 3-chloro-1-propanol; yield 79%; fusion point 122°–124° C. (from isopropanol).

Example 91

7-(3-hydroxypropoxy)-6-(1-methylethoxy)-2H-1-benzopyran-2-one.

Method K; starting materials: 7-hydroxy-6-(1-methylethoxy)-2H-1-benzopyran-2-one (example 102) and 3-chloro-1-propanol; yield 80%; fusion point 92°–94° C. (from TBME).

Example 92

6-(3-hydroxypropoxy)-7-methoxy-4-methyl-2H-1-benzopyran-2-one.

Method K; starting materials: 6-hydroxy-7-methoxy-4-methyl-2H-1-benzopyran-2-one and 3-chloro-1-propanol; yield 83%; fusion point 169°–170.5° C. (from isopropanol and water).

Example 93

6-(3-hydroxypropoxy)-7-methoxy-3,4-dimethyl-2H-1-benzopyran-2-one.

Method K; starting materials: 6-hydroxy-7-methoxy-3,4-dimethyl-2H-1-benzopyran-2-one (example 103) and 3-chloro-1-propanol; yield 82%; fusion point 160°–161° C. (from isopropanol and ethanol).

Example 94

6-(3-hydroxypropoxy)-7-methoxy-4-propyl-2H-1-benzopyran-2-one.

Method K; starting materials: 6-hydroxy-7-methoxy-4-propyl-2H-1-benzopyran-2-one (example 106) and 3-chloro-1-propanol; yield 73%; fusion point 97°–98° C. (from isopropanol and ethanol).

Example 95

6-(3-hydroxypropoxy)-7-methoxy-4-phenyl-2H-1-benzopyran-2-one.

Method K; starting materials: dalbergin and 3-chloro-1-propanol; yield 85%; fusion point 164°–165° C. (from isopropanol).

Example 96

7,8,9,10-tetrahydro-2-(3-hydroxypropoxy)-3-methoxy-6H-dibenzo[b,d]pyran-6-one.

Method K; starting materials: 7,8,9,10-tetrahydro-2-hydroxy-3-methoxy-6H-dibenzo[b,d]pyran-6-one (example 110) and 3-chloro-1-propanol; yield 74%; fusion point 176°–177° C. (from isopropanol, ethanol and acetone).

Example 97

2,3-dihydro-8-(2-hydroxyethoxy)-7-methoxy-cyclopenta[c][1]benzopyran-4(1H)-one.

Method J; starting materials: 2,3-dihydro-8-hydroxy-7-methoxycyclopenta[c][1]benzopyran-4(1H)-one (example 109) and 2-bromoethanol; yield 95%; fusion point 159°–160° C. (from ethanol).

Example 98

2,3-dihydro-8-(3-hydroxypropoxy)-7-methoxy-cyclopenta[c][1]benzopyran-4(1H)-one.

Method J (but using potassium hydrogencarbonate); Starting materials: 2,3-dihydro-8-hydroxy-7-methoxycyclopenta[c][1]benzopyran-4(1H)-one (example 109) and 3-chloro-1-propanol; yield 58%; fusion point 213°–215° C. (from isopropanol).

Example 99

2,3-dihydro-8-(4-hydroxybutyloxy)-7-methoxy-cyclopenta[c][1]benzopyran-4(1H)-one.

Method J; starting materials: 2,3-dihydro-8-hydroxy-7-methoxycyclopenta[c][1]benzopyran-4(1H)-one (example 109) and 4-chloro-1-butanol; yield 79%; fusion point 142°–143° C. (from ethyl acetate and petroleum ether).

V. Examples 100 to 110 of Intermediates of the General Formula VI

Example 100

7-ethoxy-6-hydroxy-2H-1-benzopyran-2-one. 110 g (300 mmol) esculine×1.5 H2O, 70 g (450 mmol) ethyl iodide and 82.8 g (600 mmol) of potassium carbonate are agitated in 400 ml DMF for 30 h at 85° C. This was followed by filtration, reduction of the filtrate to approximately 250 ml, the addition of approximately 200 ml ethanol and crystallization at 0° C. The crystals were boiled in 800 ml of 2N sulfuric acid for 5 h under reflux. The product was vacuum filtered, washed with water and recrystallized from water and ethanol: yield 43.2 g (70%), fusion point 145° to 146° C.

Example 101

6-(cyclopentyloxy)-7-hydroxy-2H-1-benzopyran-2-one. 50.0 g (186 mmol) of 6-hydroxy-7-phenylmethoxy-2H-1-benzopyran-2-one, 41.7 g (280 mmol) of cyclopentylbromide, 51.4 g (372 mmol) of potassium carbonate and 5.0 g of potassium iodide are agitated in 500 ml DMF for 18 h at 80° C. This is followed by filtration, evaporation, dissolution in chloroform, washing with water, drying over sodium sulfate and renewed evaporation: yield: 60.0 g (96%) of 6-(cyclopentyloxy)-7-(phenylmethoxy)-2H-1-benzopyran-2-one, fusion point 140°–141° C. (from isopropanol). Of this 15.0 g (45 mmol) in 200 ml ethanol are hydrogenated in the presence of 2.0 g Pd on active carbon (5%) for 3 h at 25° C. and 7 bar hydrogen pressure. After filtration the solvent is removed: yield 9.0 g (82%), fusion point 154°–155° C. (from isopropanol and TBME).

Example 102

7-hydroxy-6-(1-methylethoxy)-2H-1-benzopyran-2-one.

50.0 g (186 mmol) 6-hydroxy-7-phenylmethoxy-2H-1-benzopyran-2-one, 36.3 ml (387 mmol) isopropylbromide, 51.5 g (373 mmol) potassium carbonate and 5.0 g potassium iodide are agitated in 500 ml DMF for 14 h at 80° C. After filtration the filtrate is evaporated and the product recrystallized from isopropanol, yield: 57.7 g (100%) 6-(1-methyl-ethoxy)-7-(phenylmethoxy)-2H-1-benzopyran-2-one. Of this 50.0 g (161 mmol) are agitated in 100 ml of glacial acetic acid and 90 ml concentrated hydrochloric acid for 2.5 h at 70° C. This is followed by evaporation and purification using column chromatography on silica gel (eluent: chloroform and methanol 98/2 H 95/5): 24.65 g (69%), fusion point 121°–122° C. (from isopropanol).

For the production of the compounds described in following examples 103 through 110 the following procedure was utilized:

Method L:

one equivalent of β-ketoester X was added dropwise to a solution of methoxyhydroquinone in sulfuric acid (75% in water) at 0° to 25° C. Agitation was performed for at least 30 min, the product placed on ice and vacuum filtered.

Example 103

6-hydroxy-7-methoxy-3,4-dimethyl-2H-1-benzopyran-2-one.

Method L; starting material: 2-methylacetoacetic acid ethyl ester: yield 79%; fusion point 226°–229° C. (from isopropanol, ethanol and methanol).

Example 104

6-hydroxy-7-methoxy-4-(trifluoromethyl)-2H-1-benzopyran-2-one.

Method L; starting material: ethyl 4,4,4-trifluoroacetoacetic acid ethyl ester; yield 13%; fusion point 190°–192° C. (from TBME and petroleum ether).

Example 105

6-hydroxy-7-methoxy-4-(1-methylethyl)-2H-1-benzopyran-2-one.

Method L; starting material: 4-methyl-3-oxopentanoic acid methyl ester: yield 39%; fusion point 126°–127° C. (from TBME and isopropanol).

Example 106

6-hydroxy-7-methoxy-4-propyl-2H-1-benzopyran-2-one.

Method L; starting material: 3-oxohexanoic acid ethyl ester: yield 68%; fusion point 163°–164° C. (from isopropanol and ethanol).

Example 107

3-butyl-6-hydroxy-7-methoxy-4-methyl-2H-1-benzopyran-2-one.

Method L; starting material: 2-butylacetoacetic acid ethyl ester: yield 59%; fusion point 174°–175° C. (from ethanol).

Example 108

6-hydroxy-7-methoxy-4-methyl-3-phenyl-2H-1-benzopyran-2-one.

Method L; starting material: 2-phenylacetoacetic acid ethyl ester: yield 99%; fusion point 258°–260° C. (from ethanol).

Example 109

2,3-dihydro-8-hydroxy-7-methoxy-cyclopenta[c][1]benzopyran-4(1H)-one.

Method L; starting material: cyclopentanone-2-carboxylic acid ethyl ester; yield 71%; fusion point 254°–255° C. (from isopropanol).

Example 110

7,8,9,10-tetrahydro-2-hydroxy-3-methoxy-6H-dibenzo[b,d]pyran-6-one.

Method L; starting material: cyclohexanone-2-carboxylic acid ethyl ester: yield 86%; fusion point 184°–186° C. (from isopropanol).

Pharmacological Investigations

In order to determine the neuroprotective and anticonvulsive activity of the compounds in accordance with the invention of the general formula I, two slightly different methods were employed as follows:

1. In order to determine the neuroprotective efficacy NMDA at a rate of 25 mg/kg/10 ml was administered intravenously to male NMRI mice with a body weight of 20 to 25 g. As a consequence of this application the animals suffer clonic and partly tonic convulsions, which lead to death. As a criterion for the efficacy of the investigated compounds prevention of death is used.
2. In order to ascertain the antiepileptic efficacy the same method was utilized with an NMDA dosage of 40 mg/kg/10 ml i.v. This higher NMDA dosage led in the case of all animals to the occurrence of tonic convulsions.

All animals used in the investigations had free access to food and water prior to the experiments. The test and reference substances were all administered as a suspension in 0.2% agar or water, partly by the intermediary of solution promoters such as for instance PEG-400, perorally using an esophageal probe. Control animals received the same volumes of the solvent with optional solution promoters. One hour after the application of the substance NMDA was administered intravenously and the animals observed for the occurrence of convulsions.

In table 1 the results of the tests (NMDA 25 mg i.v.) performed in accordance with method 1 are compiled with dosages of 5–100 mg of the compounds in accordance with the invention per kg of body weight as compared with known NMDA-antagonists. As a percentage efficacy the percentage of surviving animals is used.

In table 2 the results of the tests (NMDA 40 mg i.v.) performed in accordance with method 2 are compiled with dosages of 5–25 mg of the compounds in accordance with the invention per kg of body weight in comparison with known anticonvulsants and antiepileptics. As a percentage efficacy the percentage of animals is used which in the test were protected against the occurrence of tonic convulsions.

The tables 1 and 2 furthermore include those doses expressed as $ED_{50}$ values, of the substances according to the present invention and of other NMDA antagonists, which in the NMDA i. v. test (25 and, respectively, 40 mg/kg) had protected 50% of the animals one hour after application against NMDA-induced death or tonic convulsions.

The determination of the $ED_{50}$ values was performed in accordance with the method described in Lichtfield and Wilcoxon, J. Pharmacol. exp. Therapeut. 96, 99 (1949) in each case with 4 to 5 groups of 10 animals per dosage rate.

During the entire period of testing the animals were observed for signs of substance-induced modifications of behavior and neurotoxicity. In the case of all compounds in accordance with the invention using the given dosages no signs of inherent toxic action were observed. Up to a dosage of 200 mg/kg no mortality occurred.

The determination of the antiallergic and anti-inflammatory properties of the compounds in accordance with the invention was using a passive rat paw anaphylaxy model. This pharmacological model is an accepted standard method for the investigation of type I hypersensitivity reactions (Martel, R. and Klicius, J., Int. Archs. Allergy Appl. Immun. 55, 205 to 209 (1977), Nolan, J. C. et al., Agents and Actions 31, 210 to 218 (1990) and Walsh, D. A. et al., J Med. Chem. 33, 1823 to 1827 (1990)). As is the case with allergic disorders of man passive rat anaphylaxy reactions involve a large number of mediators, as for instance histamine, serotonine, leucotriene, the platelet activating factor, and the like (Weg, V. B. et al., Eur. J. Pharmacol. 204, 157 to 163 (1991)).

Male Sprague-Dawley rats were utilized for all tests. The animals were kept under standardized environmental conditions with free access to food and water. For sensitization to the antigen 100 µl of a mouse antiserum to ovalbumin was injected sublplantarly into the left rear paw. The anti-body was in this respect used with a dilution, of which it was known from tests that it caused a significant paw edema. The opposite paw was for control injected subplantarly only with 100 µl of the solvent (sterile physiological NaCl solution). Overnight the investigated animals were deprived of food but had water ad lib.

The following morning the animals were treated with the aid of an esophageal probe perorally with test, reference or control substances in 10 ml/kg 0.2% agar, to which in part solution promotor had been added. Per group in all tests between 6 and 8 animals were used. One hour later the anaphylactic reaction was caused by the intravenous injection of 10 mg/10 ml/kg ovalbumin in physiological NaCl solution. After thirty minutes the volumes of both rear paws were measured plethysmographically (using a 2060 volumeter from Rhema- Labortechnik, Hofheim). The edema volume was calculated from the difference between the values of the two paws. All values found are listed in the table 3. The antiallergic action is in this case expressed as a percentage inhibition of the edema volume of the animals in the test group as compared with control groups undergoing parallel investigation. In table 3 the results of testing known antiallergics are included additionally. The determination of the $ED_{50}$ values was performed by linear regression after log transformation of the administered doses, at least three dosage rates being employed.

TABLE 1

| | NMDA Test (25 mg/kg i.v.) | | | |
|---|---|---|---|---|
| Substance of example number | Dose p.o. (mg/kg) 1 h before test | No. of animals in test | Protective action % | $ED_{50}$ (mg/kg p. o.) |
| 1 | 25 | 8 | 100 | |
| 2 | 25 | 8 | 100 | |
| 3 | 5 | 8 | 62.5 | |
| 4 | 25 | 8 | 100 | 1.7 |
| 5 | 25 | 8 | 87.5 | |
| 6 | 25 | 8 | 87.5 | 13.5 |
| 7 | 5 | 8 | 100 | 0.9 |
| 8 | 100 | 8 | 62.5 | |
| 9 | 25 | 8 | 50 | |
| 10 | 25 | 8 | 75 | 23 |
| 11 | 25 | 8 | 62.5 | |
| 12 | 25 | 8 | 62.5 | |
| 13 | 25 | 8 | 100 | |
| 14 | 25 | 8 | 37.5 | |
| 15 | 25 | 8 | 50 | |
| 16 | 100 | 8 | 75 | |
| 17 | 100 | 8 | 37.5 | |
| 18 | 25 | 8 | 100 | 6.4 |
| 19 | 25 | 8 | 100 | 8.3 |
| 20 | 50 | 8 | 87.5 | |
| 21 | 50 | 8 | 62.5 | |
| 22 | 100 | 8 | 37.5 | |
| 23 | 100 | 8 | 100 | 28.5 |
| 24 | 100 | 8 | 37.5 | |
| 25 | 100 | 8 | 100 | 77 |
| 26 | 25 | 8 | 62.5 | |
| 27 | 25 | 8 | 50 | |
| 28 | 25 | 8 | 87.5 | |
| 29 | 25 | 8 | 87.5 | |
| 30 | 100 | 8 | 37.5 | |
| 31 | 25 | 8 | 87.5 | |
| 32 | 25 | 8 | 62.5 | |
| 33 | 25 | 8 | 100 | 4.4 |
| 34 | 25 | 8 | 75 | |
| 35 | 5 | 8 | 75 | |
| 36 | 25 | 8 | 50 | |
| 37 | 25 | 8 | 100 | |
| 38 | 25 | 8 | 87.5 | |
| 39 | 25 | 8 | 62.5 | |
| 40 | 100 | 8 | 37.5 | |
| 41 | 5 | 8 | 87.5 | 4.8 |
| 42 | 25 | 8 | 100 | |
| 43 | 25 | 8 | 100 | 5.5 |
| 44 | 25 | 8 | 87.5 | 4.8 |
| 45 | 25 | 8 | 100 | 1.2 |
| 46 | 25 | 8 | 100 | 3.9 |
| 47 | 5 | 8 | 62.5 | |
| 48 | 5 | 8 | 100 | 4.0 |
| 49 | 25 | 8 | 75 | 6.8 |
| 50 | 25 | 8 | 87.5 | |
| 51 | 5 | 8 | 12.5 | |
| 52 | 25 | 8 | 100 | 1.2 |
| 53 | 25 | 8 | 50 | |
| 54 | 5 | 8 | 100 | 0.4 |
| 55 | 5 | 8 | 100 | 1.1 |
| 56 | 5 | 8 | 87.5 | 2.6 |
| 57 | 5 | 8 | 100 | |
| 58 | 5 | 8 | 100 | 1.8 |
| 59 | 5 | 8 | 100 | 1.1 |
| 60 | 5 | 8 | 62.5 | |
| 61 | 100 | 8 | 25 | |
| 62 | 25 | 8 | 87.5 | |
| 63 | 25 | 8 | 12.5 | |

TABLE 1-continued

| | NMDA Test (25 mg/kg i.v.) | | | |
|---|---|---|---|---|
| Substance of example number | Dose p.o. (mg/kg) 1 h before test | No. of animals in test | Protective action % | $ED_{50}$ (mg/kg p. o.) |
| 64 | 25 | 8 | 75 | |
| 65 | 100 | 8 | 12.5 | |
| 66 | 5 | 8 | 100 | |
| Comparative substances: | | | | |
| flunarizin | 50 | 8 | 100 | 22.8 |
| nimodipin | 20 | 8 | 87.5 | 18.5 |
| verapamil | 20 | 8 | 87.5 | 17.3 |
| dextromethorphan | 50 | 8 | 50 | 66.7 |
| ketamine | 20 | 8 | 0 | |

TABLE 2

| | NMDA Test (40 mg/kg i.v.) | | | |
|---|---|---|---|---|
| Substance of example number | Dose p.o. (mg/kg) 1 h before test | No. of animals in test | Protective action % | $ED_{50}$ (mg/kg p.o.) |
| 6 | 25 | 8 | 0 | |
| 10 | 5 | 8 | 25.0 | |
| 4 | 5 | 8 | 62.5 | |
| 49 | 20 | 8 | 87.5 | 4.0 |
| 43 | 5 | 8 | 37.5 | |
| 18 | 25 | 8 | 100 | |
| 19 | 25 | 8 | 87.5 | |
| 23 | 5 | 8 | 12.5 | |
| Comparative substances: | | | | |
| flunarizin | 50 | 8 | 100 | |
| nimodipin | 20 | 8 | 25 | 25.4 |
| verapamil | 50 | 8 | 50 | |
| dextromethorphan | 100 | 8 | 100 | 58 |
| diazepam | 5 | 8 | 25 | |
| valproinic acid | 250 | 8 | 87.5 | |
| carbamazepin | 50 | 8 | 75 | |
| diphenylhydantoin | 50 | 8 | 50 | |
| phenobarbital | 50 | 8 | 62.5 | |

TABLE 3

| | Passive rat paw anaphylaxy | | |
|---|---|---|---|
| Substance of example number | Dose p.o. (mg/kg) 1 h before test | Protective action % | $ED_{50}$ (mg/kg p.o.) |
| 4 | 25 | 79 | |
| 8 | 25 | 35 | |
| 10 | 25 | 22 | |
| 12 | 25 | 12 | |
| 14 | 25 | 81* | 2.4 |
| 15 | 25 | 60 | |
| 16 | 25 | 60 | |
| 17 | 25 | 83 | |
| 18 | 25 | 56 | |
| 19 | 25 | 32 | |
| 25 | 25 | 43 | |
| 26 | 25 | 66 | |
| 27 | 25 | 40 | |
| 28 | 25 | 72 | |
| 39 | 25 | 26 | |
| 40 | 25 | 27 | |
| 42 | 25 | 39 | |
| 43 | 25 | 19 | |
| 45 | 25 | 69 | |
| 46 | 25 | 35 | |
| 48 | 25 | 35 | |
| 49 | 25 | 47 | |
| 52 | 25 | 74 | |
| Comparative substances: | | | |
| astemizole | 10 | 70 | 3.1 |
| cromoglycate* | 2.25 | 58 | 1.1 |
| diphenhydramine | 100 | 54 | 73 |
| ketotifen | 30 | 77 | 5.6 |
| oxatomide | 30 | 75 | 7.3 |

TABLE 3-continued

| | Passive rat paw anaphylaxy | | |
|---|---|---|---|
| Substance of example number | Dose p.o. (mg/kg) 1 h before test | Protective action % | $ED_{50}$ (mg/kg p.o.) |
| picumast | 25 | −21 | — |
| theophylline | 60 | 58 | 41.2 |

*Action remains for a period of 24 hours with full effect

*Intravenous treatment was performed immediately prior to test, orally not effective.

Examples for the production of pharmaceutical preparations of the substances in accordance with the invention:

A. Tablets

For the manufacture of tablets, which dependent on the desired activity contained 5 to 250 mg of active principle, the following are required:

| | |
|---|---|
| compound acc. to the invention (active principle) | 200 to 5000 g |
| cellulose powder | 2000 g |
| corn starch | 1200 g |
| colloidal silicic acid | 80 g |
| magnesium stearate | 20 g |
| lactose | ad 10000 g |

If necessary the active principle was ground, homogeneously mixed with the adjuvant materials and pressed to tablets each weighing 250 mg and having a diameter of 9 mm, but in the case of dosages of over 125 mg the tablets were pressed with a weight of 500 mg and a diameter of 11 mm. If desired the tablets were provided with a film coating.

B. Capsules:

For the production of capsules, which dependent on the desired potency contained 5 to 250 mg of active principle, the following are necessary:

| | |
|---|---|
| compound acc. to the invention (active principle) | 500 to 12500 g |
| corn starch | 2000 g |
| colloidal silica gel | 300 g |
| magnesium stearate | 50 g |
| cellulose powder | ad 20000 g |

The finely powdered substances are homogeneously mixed and filled into No. 2 hard gelatine casings at a rate of 200 mg per capsule, or in the case of dosages of over 125 mg into No. 0 hard gelatine casings at a rate of 400 mg per capsule.

We claim:

1. A 2H-1-benzopyran-2-one having the formula (I),

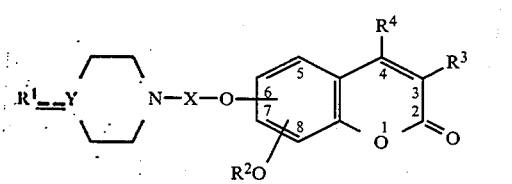

wherein:

X denotes an alkylene group with 2 to 5 C atoms or a 2-hydroxypropylene group,

Y denotes a nitrogen atom, a CH— group, a COH— group or a carbon atom, $R^1$ denotes a phenyl, benzhydryl, benzhydrylidene, benzyl, diphenylhydroxymethyl, pyridinyl or pyrimidinyl radical, which is optionally substituted with respectively one or two $C_1$–$C_5$ alkyl groups, with respectively one or two halogen atoms, with halogen and simultaneously $C_1$–$C_5$ alkyl, with perfluoroalkyl with 1 to 3 C atoms, $C_1$–$C_5$ alkoxy, methylenedioxy, hydroxy, or nitro, $R^2$ denotes a straight chained or branched alkyl radical with 1 to 5 C atoms or a cycloalkyl radical with 4 to 6 C atoms, $R^3$ denotes a hydrogen atom, an alkyl group with 1 to 4 C atoms or a phenyl radical, $R^4$ denotes a hydrogen atom, an alkyl group with 1 to 4 C atoms, a phenyl radical or a trifluoromethyl radical or $R^3$ and $R^4$ jointly denote a polymethylene chain —$(CH_2)_n$— with n equal to 3 or 4, and the pharmaceutically-acceptable salts thereof.

2. A compound as claimed in claim 1 wherein, in said formula (I),

X denotes an alkylene group with 2 to 5 C atoms,

Y denotes N or CH, $R^1$ denotes a phenyl or diphenylhydroxymethyl radical with optional substitution by a halogen atom, methyl, methoxy, ethoxy, or hydroxy, $R^2$ denotes methyl or ethyl, $R^3$ denotes a hydrogen atom or a methyl or phenyl group, $R^4$ denotes a hydrogen atom, methyl, propyl, isopropyl or $R^3$ and $R^4$ jointly denote a polymethylene chain —$(CH_2)_n$— in which n is equal to 3 or 4, and the pharmaceutically-acceptable salts thereof.

3. A reactive intermediate having the formula (XI):

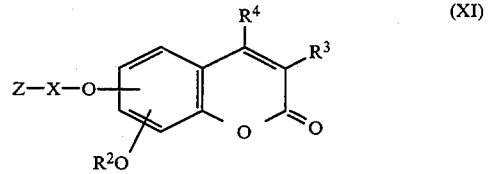

wherein:

$R^2$ denotes a straight chained or branched alkyl radical with 1 to 5 C atoms or a cycloalkyl radical with 4 to 6 C atoms, $R^3$ denotes a hydrogen atom, an alkyl group with 1 to 4 C atoms or a phenyl radical, $R^4$ denotes a hydrogen atom, an alkyl group with 1 to 4 C atoms, a phenyl radical or a trifluoromethyl radical or $R^3$ and $R^4$ jointly denote a polymethylene chain —$(CH_2)_n$— with n equal to 3 or 4

X denotes an alkylene group with 2 to 5 C atoms and

Z denotes a hydroxyl group or a methanesulfonyloxy group, a halogen atom or

Z—X jointly denote an oxiranylmethylene group with the exclusion of 7-methoxy-6-(oxiranylmethoxy)-2H-1-benzopyran-2-one and 7-methoxy-4-methyl-6-(oxiranylmethoxy)-2H-1-benzopyran-2-one.

4. A pharmaceutical preparation comprising at least one compound as claimed in claim 1 or claim 2 in an amount sufficient to provide NMDA-antagonistic neuroprotective action, together with pharmaceutically-acceptable carriers.

5. A method for preventing or treating NMDA-induced convulsions in humans comprising the administration to a person in need of such treatment of a safe and effective amount of the compound of claim 1.

* * * * *